(12) United States Patent
Kaplan

(10) Patent No.: US 10,093,746 B2
(45) Date of Patent: Oct. 9, 2018

(54) GLYPICAN-3 ANTIBODY AND USES THEREOF

(71) Applicants: THE TRUSTEES OF THE UNIVERSITY OF PENNSYLVANIA, Philadelphia, PA (US); The United States of America as represented by the Department of Veterans Affairs, Washington, DC (US)

(72) Inventor: David Kaplan, Media, PA (US)

(73) Assignees: The Trustees of the University of Pennsylvania, Philadelphia, PA (US); The United States of America as represented by the Department of Veterans Affairs, Washington, DC (US)

( * ) Notice: Subject to any disclaimer, the term of this patent is extended or adjusted under 35 U.S.C. 154(b) by 31 days.

(21) Appl. No.: 15/508,317

(22) PCT Filed: Sep. 3, 2015

(86) PCT No.: PCT/US2015/048391
§ 371 (c)(1),
(2) Date: Mar. 2, 2017

(87) PCT Pub. No.: WO2016/036973
PCT Pub. Date: Mar. 10, 2016

(65) Prior Publication Data
US 2017/0291954 A1   Oct. 12, 2017

Related U.S. Application Data

(60) Provisional application No. 62/045,875, filed on Sep. 4, 2014, provisional application No. 62/045,641, filed on Sep. 4, 2014.

(51) Int. Cl.
| C07K 14/725 | (2006.01) |
| C07K 16/30 | (2006.01) |
| A61K 35/17 | (2015.01) |
| G01N 33/574 | (2006.01) |
| A61K 35/12 | (2015.01) |

(52) U.S. Cl.
CPC .......... *C07K 16/303* (2013.01); *A61K 35/17* (2013.01); *C07K 14/7051* (2013.01); *G01N 33/57438* (2013.01); *A61K 2035/124* (2013.01); *C07K 2317/21* (2013.01); *C07K 2317/24* (2013.01); *C07K 2317/54* (2013.01); *C07K 2317/55* (2013.01); *C07K 2317/569* (2013.01); *C07K 2317/622* (2013.01); *C07K 2319/02* (2013.01); *C07K 2319/03* (2013.01); *G01N 2333/705* (2013.01)

(58) Field of Classification Search
CPC .. C07K 14/7051; C07K 16/303; A61K 35/17; G01N 33/57438
See application file for complete search history.

(56) References Cited

U.S. PATENT DOCUMENTS

| 6,410,319 | B1 | 6/2002 | Raubitschek et al. |
| 7,919,086 | B2 * | 4/2011 | Nakano ................ C07K 16/303 |
| | | | 424/133.1 |
| 2007/0190599 | A1 | 8/2007 | Nakano et al. |
| 2010/0209432 | A1 | 8/2010 | Terrette et al. |
| 2010/0239577 | A1 | 9/2010 | Igawa et al. |
| 2010/0248359 | A1 | 9/2010 | Nakano et al. |
| 2014/0044714 | A1 | 2/2014 | Ho et al. |
| 2014/0170114 | A1 | 6/2014 | Kaplan et al. |
| 2016/0215261 | A1 * | 7/2016 | Li ........................ C12N 5/0638 |

FOREIGN PATENT DOCUMENTS

| WO | WO-2014180306 A1 * | 11/2014 | .......... C12N 5/0638 |
| WO | WO-2017172981 A2 * | 10/2017 | .......... A61K 48/005 |

OTHER PUBLICATIONS

Zhu et al., Clin Cancer Res 19(4):920-8 (Year: 2012).*
International Search Report and Written Opinion for PCT International Application No. PCT/US2015/048391 dated Dec. 14, 2015.
Aburatani, "Discovery of a new biomarker for gastroenterological cancers", J Gastroenterol. 40 Suppl 16, 2005, 1-6.
Anatelli, et al., "Value of glypican 3 immunostaining in the diagnosis of hepatocellular carcinoma on needle biopsy", Am J Clin Pathol. 130(2), 2008, 219-223.
Baumhoer, et al., "Glypican 3 expression in human nonneoplastic, preneoplastic, and neoplastic tissues: a tissue microarray analysis of 4,387 tissue samples", Am J Clin Pathol. 129(6), 2008, 899-906.
Capurro, et al., "Glypican-3 as a serum marker for hepatocellular carcinoma", Cancer Res. 65(1), 2005, 372-373.
Capurro, et al., "Glypican-3: a novel serum and histochemical marker for hepatocellular carcinoma", Gastroenterology. 125(1), 2003, 89-97.
Feng, et al., "Glypican-3 antibodies: a new therapeutic target for liver cancer", FEBS Lett. 588(2), 2014, 377-382.
Feng, et al., "Recombinant soluble glypican 3 protein inhibits the growth of hepatocellular carcinoma in vitro", Int J Cander. 128(9), 2011, 2246-2247.
Hippo, et al., "Identification of soluble NH2-terminal fragment of glypican-3 as a serological marker for early-stage hepatocellular carcinoma", Cancer Res. 64(7), 2004, 2418-2423.

(Continued)

*Primary Examiner* — Jessica H Roark
(74) *Attorney, Agent, or Firm* — Saul Ewing Arnstein & Lehr, LLP; Kathryn Doyle

(57) ABSTRACT

The present invention relates to compositions and methods of isolated polynucleotides that encode or polypeptides comprising glypican-3 (GPC3). The invention also includes a chimeric antigen receptor (CAR) wherein the CAR is able to target GPC3. The invention further includes methods of treating a subject or diagnosing and treating diseases, disorders or conditions associated with dysregulated glypican-3.

23 Claims, 11 Drawing Sheets
Specification includes a Sequence Listing.

(56) References Cited

OTHER PUBLICATIONS

Li, et al., "T-Cells Transduced With Human Glypican-3 Specific Chimeric Antigen Receptor Specifically Lyse Hepatocellular Carcinoma Cell Line In Vitro", Hepatology. 54(4) Suppl. AASLD Abstracts, 2011, 1279A.

Li, et al., "Validation of glypican-3-specific scFv isolated from paired display/secretory yeast display library", BMC Biotechnol. 12, 2012, 23.

Nakano, et al., "Generation of a humanized anti-glypican 3 antibody by CDR grafting and stability optimization", Anticancer Drugs. 21(10), 2010, 907-916 (abstract only).

Ruan, et al., "Inhibition of glypican-3 expression via RNA interference influences the growth and invasive ability of the MHCC97-H human hepatocellular carcinoma cell line", Int J Mol Med. Oct. 2011;28(4), 2011, 497-503.

Sun, et al., "Suppression of glypican 3 inhibits growth of hepatocellular carcinoma cells through up-regulation of TGF-32", Neoplasia. 13(8), 2011, 735-747.

Takai, et al., "Involvement of glypican-3 in the recruitment of M2-polarized tumor-associated macrophages in hepatocellular carcinoma.", Cancer Biol Ther. 8(24), 2009, 2329-2338.

Zittermann, et al., "Soluble glypican 3 inhibits the growth of hepatocellular carcinoma in vitro and in vivo", Int J Cancer. 126(6), 2010, 1291-1301.

* cited by examiner

```
                              SEQUENCE LISTING

<160> NUMBER OF SEQ ID NOS: 17

<210> SEQ ID NO 1
  <211> LENGTH: 345
  <212> TYPE: DNA
  <213> ORGANISM: Mus musculus

<400> SEQUENCE: 1
caggttcaac tgcagcagtc tggggctgag ctggtgaggc ctggggcttc agtgaagctg      60
tcctgcaagg cttcgggcta cacatttaat gactatgaaa tgcactgggt gaagcagaca     120
cctgtgcatg gcctaaaatg gattggagct cttgagccta aaactggtga tactgcctac     180
agtcagaagt tcaagggcaa ggccacactg actgcagaca atcctccag cacagcctac      240 atggagctcc gcagcctgac atctgaggac tctgccgtct attactgtac cagctgctac     300
tactatactt actcgggcca agggactctg gtcactgtct ctgca                     345

<210> SEQ ID NO 2
  <211> LENGTH: 115
  <212> TYPE: PRT
  <213> ORGANISM: Mus musculus

<400> SEQUENCE: 2

Gln Val Gln Leu Gln Gln Ser Gly Ala Glu Leu Val Arg Pro Gly Ala
  1               5                   10                  15

Ser Val Lys Leu Ser Cys Lys Ala Ser Gly Tyr Thr Phe Asn Asp Tyr
                  20                  25                  30

Glu Met His Trp Val Lys Gln Thr Pro Val His Gly Leu Lys Trp Ile
              35                  40                  45

Gly Ala Leu Glu Pro Lys Thr Gly Asp Thr Ala Tyr Ser Gln Lys Phe
          50                  55                  60

Lys Gly Lys Ala Thr Leu Thr Ala Asp Lys Ser Ser Ser Thr Ala Tyr
  65                  70                  75                  80

Met Glu Leu Arg Ser Leu Thr Ser Glu Asp Ser Ala Val Tyr Tyr Cys
                  85                  90                  95

Thr Ser Cys Tyr Tyr Tyr Thr Tyr Ser Gly Gln Gly Thr Leu Val Thr
                  100                 105                 110

Val Ser Ala
          115

<210> SEQ ID NO 3
  <211> LENGTH: 336
  <212> TYPE: DNA
  <213> ORGANISM: Mus musculus

<400> SEQUENCE: 3
gatgttgtga tgacccaaac tccactctcc ctgcctgtca gtcttggaga tcaagcctcc      60
atctcttgca gatctagtca gagccttgta cacagtaatg gaaacaccta tttacattgg     120
tacctgcaga agccaggcca gtctccaaag ctcctgatct acaaagtttc caaccgattt     180
tctggggtcc cagacaggtt cagtgcagt ggatcaggga cagatttcac actcaagatc     240
```
agcagagtgg aggctgagga tctgggagtt tatttctgct ctcaaaatac acctgttcct    300
cctaagttcg gatcggggac caagctggaa ataaaa    336

<210> SEQ ID NO 4
<211> LENGTH: 112
<212> TYPE: PRT
<213> ORGANISM: Mus musculus

<400> SEQUENCE: 4

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr Pro Val Pro Pro Lys Phe Gly Ser Gly Thr Lys Leu Glu Ile Lys
            100                 105                 110

<210> SEQ ID NO 5
<211> LENGTH: 75
<212> TYPE: DNA
<213> ORGANISM: Mus musculus

<400> SEQUENCE: 5
caggttcaac tgcagcagtc tggggctgag ctggtgaggc ctggggcttc agtgaagctg    60
tcctgcaagg cttcg    75

<210> SEQ ID NO 6
<211> LENGTH: 24
<212> TYPE: DNA
<213> ORGANISM: Mus musculus

<400> SEQUENCE: 6
ggctacacat ttaatgacta tgaa    24

<210> SEQ ID NO 7
<211> LENGTH: 51
<212> TYPE: DNA
<213> ORGANISM: Mus musculus

<400> SEQUENCE: 7
atgcactggg tgaagcagac acctgtgcat ggcctaaaat ggattggagc t    51

<210> SEQ ID NO 8
<211> LENGTH: 24
<212> TYPE: DNA
<213> ORGANISM: Mus musculus

<400> SEQUENCE: 8
cttgagccta aaactggtga tact    24

<210> SEQ ID NO 9
<211> LENGTH: 114

<212> TYPE: DNA
<213> ORGANISM: Mus musculus

<400> SEQUENCE: 9
gcctacagtc agaagttcaa gggcaaggcc acactgactg cagacaaatc ctccagcaca        60
gcctacatgg agctccgcag cctgacatct gaggactctg ccgtctatta ctgt              114

<210> SEQ ID NO 10
<211> LENGTH: 54
<212> TYPE: DNA
<213> ORGANISM: Mus musculus

<400> SEQUENCE: 10
accagctgct actactatac ttactcgggc caagggactc tggtcactgt ctct              54

<210> SEQ ID NO 11
<211> LENGTH: 78
<212> TYPE: DNA
<213> ORGANISM: Mus musculus

<400> SEQUENCE: 11
gatgttgtga tgacccaaac tccactctcc ctgcctgtca gtcttggaga tcaagcctcc        60
atctcttgca gatctagt                                                      78

<210> SEQ ID NO 12
<211> LENGTH: 34
<212> TYPE: DNA
<213> ORGANISM: Mus musculus

<400> SEQUENCE: 12
cagagccttg tacacagtaa tggaaacacc tatt                                    34

<210> SEQ ID NO 13
<211> LENGTH: 51
<212> TYPE: DNA
<213> ORGANISM: Mus musculus

<400> SEQUENCE: 13
ttacattggt acctgcagaa gccaggccag tctccaaagc tcctgatcta c                 51

<210> SEQ ID NO 14
<211> LENGTH: 9
<212> TYPE: DNA
<213> ORGANISM: Mus musculus

<400> SEQUENCE: 14 aaagtttcc                                                                9

<210> SEQ ID NO 15
<211> LENGTH: 108
<212> TYPE: DNA
<213> ORGANISM: Mus musculus

<400> SEQUENCE: 15
aaccgatttt ctggggtccc agacaggttc agtggcagtg gatcagggac agatttcaca        60
ctcaagatca gcagagtgga ggctgaggat ctgggagttt atttctgc                     108

<210> SEQ ID NO 16
<211> LENGTH: 48
<212> TYPE: DNA
<213> ORGANISM: Mus musculus

```
<400> SEQUENCE: 16
tctcaaaata cacctgttcc tcctaagttc ggatcgggga ccaagctg            48

<210> SEQ ID NO 17
<211> LENGTH: 21
<212> TYPE: PRT
<213> ORGANISM: Mus musculus

<400> SEQUENCE: 17

Arg Arg Arg Glu Leu Ile Gln Lys Leu Lys Ser Phe Ile Ser Phe Tyr
1               5                   10                  15

Ser Ala Leu Pro Gly
            20
```

GLYPICAN-3 ANTIBODY AND USES THEREOF

CROSS-REFERENCE TO RELATED APPLICATIONS

This application is a 35 U.S.C. § 371 national phase application from, and claims priority to, International Application No. PCT/US2015/048391, filed Sep. 3, 2015, and published under PCT Article 21(2) in English, which claims priority to U.S. Provisional Application Ser. No. 62/045,641 and U.S. Provisional Application Ser. No. 62/045,875, both filed on Sep. 4, 2014, the contents of which are incorporated by reference herein in their entireties.

STATEMENT REGARDING FEDERALLY SPONSORED RESEARCH OR DEVELOPMENT

This invention was made with government support under CA149908 awarded by the National Institute of Health. The government has certain rights in the invention.

BACKGROUND OF THE INVENTION

Hepatocellular carcinoma (HCC) is the fifth most common cancer and the third most common cause of cancer-related death worldwide (El-Serag, 2002, J Clin Gastroenterology 35:S72-78). During transformation from dysplastic regenerating hepatocytes to malignant hepatoma cells, several tumor-associated proteins are expressed that potentially could allow immune discrimination of malignant hepatocytes from surrounding non-tumor cells. Glypican-3 (GPC3), an oncofetal antigen re-expressed in a high frequency of neoplastic hepatocytes (Vidali, et al., 2008, J hepatol 48:399-406; Verbeeck, et al., 2008, J Clin Microbiol 46:1901-1906; Levrero, et al., 2009, J hepatol 51:581-592; Shaker, et al., 2009, Br J Dermatol 160:980-983) has emerged as a useful immunohistochemical diagnostic test (Anatelli, et al., 2008, Am J Clin Path 130:219-223; Baumhoer, et al., 2008, Am J Clin Path 129:899-906; Coston, et al., 2008, Am J Surg Pathol 32:433-444) and potential biomarker (Aburatani, 2005, J Gastroenterol 40, S16:1-6; Capurro, et al., 2005, Cancer Res 65:372; Capurro, et al., 2003, Gastroenterology 125:89-97; Hippo, et al., 2004, Cancer Res 64:2418-2423) for hepatocellular carcinoma. Glypican-3 appears critical for the association of growth factors such as IGF-2, BMP-7 and FGF-2 with growth factor receptors (Thapa, et al., 2009, J Paediatr Child Health 45:71-72; Zittermann, et al., 2010, Int J Cancer 126:1291-1301) but also may play an immunomodulatory role (Takai, et al., 2009, Cancer Biol Ther 8:2329-2338). Inhibition of glypican-3 function via knockdown (Ruan, et al., 2011, Int J Mol Med 28:497-503; Sun, et al., 2011, Neoplasia 13:735-747) or competition (Zittermann, et al., 2010, Int J Cancer 126:1291-1301; Feng, et al., 2011, Int J Cancer 128:2246-2247) has a profound negative effect on HCC cell line proliferation. Unlike any other tumor antigen associated with hepatocellular carcinoma to date, GPC3 is a glycophosphatidylinositiol-linked membrane-associated protein with a large extracellular domain attractive for antibody-directed therapy. An anti-glypican-3 antibody that induces antibody-dependent cytotoxicity has been shown to have anti-tumor effect in a xenograft animal model of hepatocellular carcinoma (Takai, et al., 2009, Cancer Biol Ther 8: 2329-38); this antibody has subsequently been humanized (Nakano, et al., 2010, Anticancer Drugs 21:907-916) and is entering human clinical trials. Thus the relative specific expressions of GPC3 on cell surface of malignant HCC tissues make it an attractive target for HCC tumor immunotherapy. However, the GPC3-specific T bodies, particularly the GPC3-specific scFv as targeting moieties, remain under development. The present invention addresses this need.

SUMMARY OF THE INVENTION

As described below, the present invention includes compositions and methods for treating, among other diseases, cancer or any malignancy or autoimmune disease in which expression of GPC3 is dysregulated.

In one aspect, the invention includes an isolated polynucleotide encoding an anti-glypican-3 (GPC3) antibody or fragment thereof comprising a heavy chain and a light chain, wherein the isolated polynucleotide encoding the heavy chain comprises SEQ ID NO: 1 and the isolated polynucleotide encoding the light chain comprises SEQ ID NO: 3.

In another aspect, the invention includes an isolated polypeptide for an anti-GPC3 antibody or fragment thereof comprising a heavy chain and a light chain, wherein the isolated polypeptide of the heavy chain comprises SEQ ID NO: 2 and the isolated polypeptide of the light chain comprises SEQ ID NO: 4.

In yet another aspect, the invention includes an isolated anti-GPC3 antibody or fragment thereof comprising a heavy chain and a light chain, wherein the isolated polypeptide specifically binds to SEQ ID NO:17.

In another aspect, the invention includes a pharmaceutical composition comprising an effective amount of the isolated polynucleotide or the isolated polypeptide described herein.

In yet another aspect, the invention includes a pharmaceutical composition comprising an effective amount of the isolated anti-GPC3 antibody or fragment thereof described herein.

In another aspect, the invention includes an isolated nucleic acid sequence encoding a chimeric antigen receptor (CAR) comprising a glypican-3 (GPC3) binding domain, a transmembrane domain, a costimulatory signaling region, and a CD3 zeta signaling domain, wherein the isolated nucleic acid sequence that encodes the GPC3 binding domain comprises SEQ ID NO: 1 and SEQ ID NO: 3.

In yet another aspect, the invention includes an isolated chimeric antigen receptor (CAR) comprising a GPC3 binding domain and a CD3 zeta signaling domain, wherein the GPC3 binding domain comprises SEQ ID NO: 2 and SEQ ID NO: 4.

In still another aspect, the invention includes a T cell comprising the isolated nucleic acid sequence or the CAR described herein.

In various embodiments of the above aspects or any other aspect of the invention delineated herein, the anti-GPC3 antibody or fragment thereof comprises an antigen-binding domain. In yet another embodiment, the antibody fragment is selected from the group consisting of a Fab fragment, a F(ab')$_2$ fragment, a Fv fragment, and a single chain Fv (scFv). In still another embodiment, the antibody or fragment thereof is selected from the group consisting of an antigen-binding (Fab), a single-chain variable fragment (scFv), a single-domain antibody, and fragment thereof.

In another embodiment, the GPC3 binding domain is an antibody or a fragment thereof, such as an antigen-binding (Fab), a single-chain variable fragment (scFv), a single-domain antibody, and fragment thereof. In yet another embodiment, the GPC3 binding domain is selected from the group consisting of a human antibody, humanized antibody, and fragment thereof. In still another embodiment, the GPC3 binding domain comprises a heavy and a light chain, such as the heavy chain comprises SEQ ID NO: 2 and the light chain comprises SEQ ID NO: 4.

Various embodiments of the above aspects or any other aspect of the invention delineated herein further comprise the sequence of a co-stimulatory signaling domain. In another embodiment, the co-stimulatory signaling domain comprises the intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

In another aspect, the invention includes a method of imaging or visualizing a sample taken from a normal or malignant tissue, the method comprising contacting the sample with a labeled anti-GPC3 antibody or fragment thereof, wherein the anti-GPC3 antibody or fragment thereof comprises a heavy chain and a light chain, wherein the heavy chain comprises SEQ ID NO: 2 and the light chain comprises SEQ ID NO: 4.

In yet another aspect, the invention includes a method for diagnosing a condition associated with expression of GPC3 in a cell, the method comprising a) contacting the cell with an anti-GPC3 antibody fragment comprising a heavy chain and a light chain, wherein the heavy chain comprises SEQ ID NO: 2 and the light chain comprises SEQ ID NO: 4; and b) detecting GPC3 expression, wherein the expression of GPC3 indicates a likelihood of a condition associated with the expression of GPC3.

In still another aspect, the invention includes a method of diagnosing, prognosing, or determining risk of liver cancer in a subject, the method comprising contacting the sample derived from the subject with an anti-GPC3 antibody fragment comprising a heavy chain and a light chain, wherein an amino acid sequence of the heavy chain comprises SEQ ID NO: 2 and the amino acid sequence of the light chain comprises SEQ ID NO: 4; and detecting GPC3 in the sample, wherein the detection of GPC3 indicates a likelihood of liver cancer in the subject.

In another aspect, the invention includes a method of inhibiting growth of a GPC3-expressing tumor cell, the method comprising contacting the tumor cell with an anti-GPC3 antibody or a fragment thereof comprising a heavy chain and a light chain, wherein an amino acid sequence of the heavy chain comprises SEQ ID NO: 2 and the amino acid sequence of the light chain comprises SEQ ID NO: 4.

In yet another aspect, the invention includes a method of providing an anti-tumor immunity in a subject, the method comprising administering to the subject an effective amount of a genetically modified cell comprising an isolated nucleic acid sequence encoding a chimeric antigen receptor (CAR) that comprises a glypican-3 (GPC3) binding domain and a CD3 zeta signaling domain, wherein the GPC3 binding domain comprises a heavy chain comprising SEQ ID NO: 2 and a light chain comprising SEQ ID NO: 4.

In still another aspect, the invention includes a method of treating a subject having a disease, disorder or condition associated with dysregulated expression of glypican-3, the method comprising administering to the subject an effective amount of a genetically modified cell comprising an isolated nucleic acid sequence encoding a chimeric antigen receptor (CAR) that comprises a GPC3 binding domain and a CD3 zeta signaling domain, wherein the GPC3 binding domain comprises SEQ ID NO: 2 and SEQ ID NO: 4.

In various embodiments of the above aspects or any other aspect of the invention delineated herein, the tissue comprises liver tissue.

In another embodiment, the cell is an autologous T cell. In yet another embodiment, the subject is a human.

In another embodiment, the disease, disorder or condition associated with dysregulated expression of GPC3 is selected from the group consisting of liver cancer, pancreatic cancer, ovarian cancer, stomach cancer, lung cancer, endometrial cancer, hepatocellular carcinoma, and any combination thereof.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION

Figure 1:
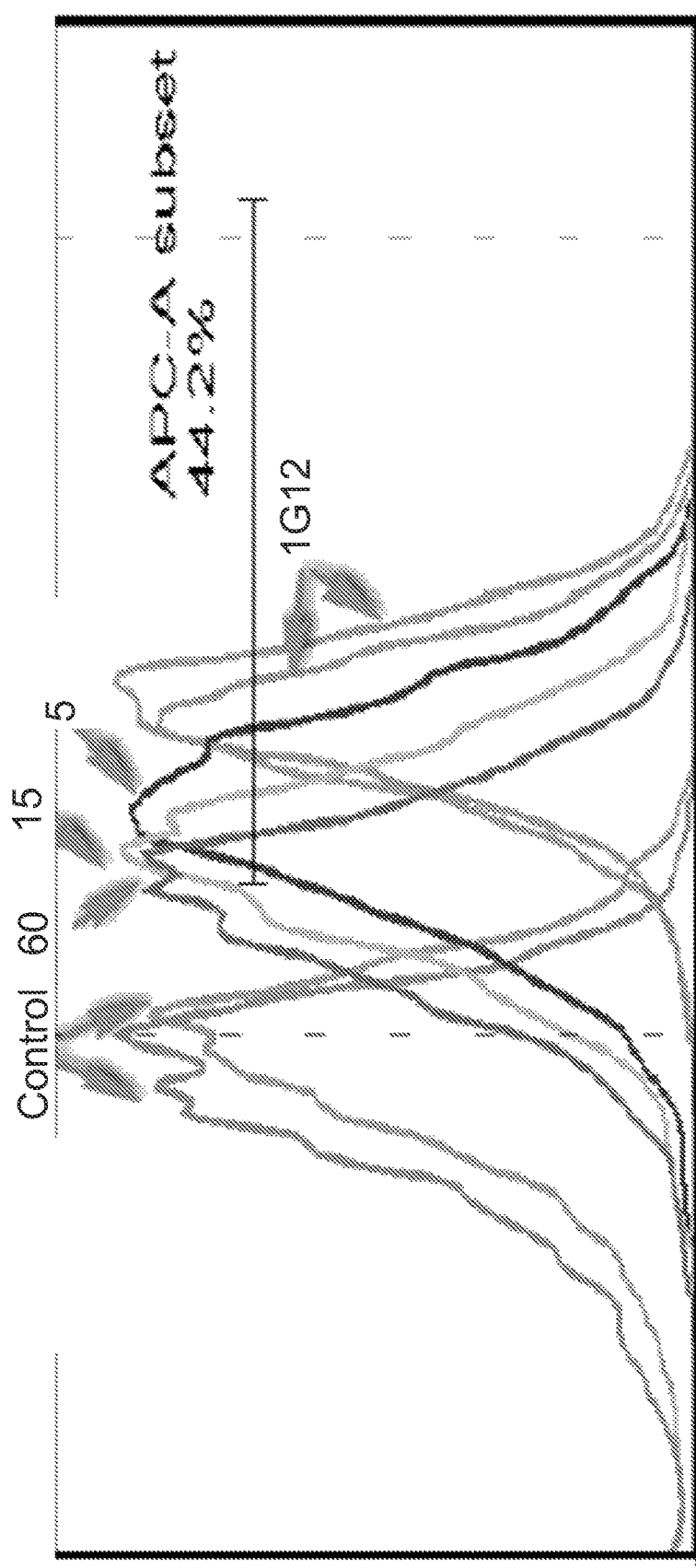
FIG. 1 is a panel of images showing anti-glypican-3 antibody (4E5) bound to glypican-3 positive cells, Huh7. 1G12, GPC3-specific IgG1 antibody, was used as a positive control.

The present invention is based partly on the identification of human-derived antibodies that specifically bind to glypican-3 (GPC3). The antibodies of the invention can be used for diagnostic and in vivo therapeutic applications. In embodiment, a peptide containing amino acids 530-558 or 368-548 of human GPC3 was used to screen a paired display/secretory yeast library to isolate human-derived scFv against GPC3.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

As used herein, the terms "glypican-3," "glypican proteoglycan 3," "GPC3," are used interchangeably, and include variants, isoforms and species homologs of human glypican-3. Accordingly, antibodies of this disclosure may cross-react with glypican-3 from species other than human, such as mouse or rat. In certain embodiments, the antibodies may be completely specific for one or more human glypican-3 proteins and may not exhibit species or other types of non-human cross-reactivity. The complete amino acid sequence of an exemplary human glypican-3 has Genbank/NCBI accession number NM004484.

"About" as used herein when referring to a measurable value such as an amount, a temporal duration, and the like, is meant to encompass variations of ±20% or ±10%, ±5%, ±1%, or ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies (scFv) and humanized antibodies (Harlow et al., 1999, In: Using Antibodies: A Laboratory Manual, Cold Spring Harbor Laboratory Press, N.Y.; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2 and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. K and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia greata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for the ability to bind glypican-3 using the functional assays described herein.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "dysregulated" when used in the context of the level of expression or activity of GPC3 refers to the level of expression or activity that is different from the expression level or activity of GPC3 in an otherwise identical healthy animal, organism, tissue, cell or component thereof. The term "dysregulated" also refers to the altered regulation of the level of expression and activity of GPC3 compared to the regulation in an otherwise identical healthy animal, organism, tissue, cell or component thereof.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "immune response" as used herein is defined as a cellular response to an antigen that occurs when lymphocytes identify antigenic molecules as foreign and induce the formation of antibodies and/or activate lymphocytes to remove the antigen.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell. An example of a "cell surface receptor" is human GPC3.

"Single chain antibodies" refer to antibodies formed by recombinant DNA techniques in which immunoglobulin heavy and light chain fragments are linked to the Fv region via an engineered span of amino acids. Various methods of generating single chain antibodies are known, including those described in U.S. Pat. No. 4,694,778; Bird (1988) Science 242:423-442; Huston et al. (1988) Proc. Natl. Acad. Sci. USA 85:5879-5883; Ward et al. (1989) Nature 334: 54454; Skerra et al. (1988) Science 242:1038-1041.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals).

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides isolated antibodies, particularly antibodies that bind specifically to human or murine glypican-3 (GPC3). In certain embodiments, the antibodies of the invention comprise particular structural features, such as CDR regions comprising particular amino acid sequences. The invention also provides methods of making such antibodies. The antibodies of the invention can be incorporated into an immunoconjugate, a chimeric antigen receptor (CAR), a pharmaceutical composition, and the like. In one embodiment, the immunoconjugates of the invention may be therapeutic agents, for example, cytotoxins or radioactive isotopes. Accordingly, the present invention provides compositions and methods for treating, among other diseases, cancer or any malignancy or autoimmune disease in which expression of GPC3 is dysregulated.

In one aspect, the invention includes an isolated nucleic acid sequence encoding a chimeric antigen receptor (CAR) comprising a glypican-3 (GPC3) binding domain, a transmembrane domain, a costimulatory signaling region, and a CD3 zeta signaling domain. Another aspect includes an isolated chimeric antigen receptor (CAR) comprising a GPC3 binding domain and a CD3 zeta signaling domain, wherein the GPC3 binding domain comprises SEQ ID NO: 2 and SEQ ID NO: 4.

In another aspect, the invention includes a cell (e.g., T cell) engineered to express a chimeric antigen receptor (CAR) wherein the CAR T cell exhibits an antitumor property. In one embodiment, the antigen is GPC3. In one embodiment, the antigen recognition domain of the CAR comprises a anti-GPC3. Accordingly, the invention provides a anti-GPC3-CAR engineered into a T cell and methods of their use for adoptive therapy.

Anti-Glypican-3 (Anti-GPC3) Antibodies

The antibodies of the invention are characterized by particular functional features or properties of the antibodies. For example, the antibodies bind specifically to glypican-3. The antibodies may bind to glypican-3 with high affinity, for example with an affinity EC50 ranging from about 5.0-110.9 nM. The antibodies of the invention may specifically recognize naturally expressed GPC3 protein, human or murine, on a cell and do not cross-react to other non-GPC3 proteoglycans.

One aspect of the invention includes an isolated polynucleotide encoding an anti-glypican-3 (GPC3) antibody or fragment thereof comprising a heavy chain and light chain. The isolated polynucleotide encoding the heavy chain comprises SEQ ID NO: 1 and the isolated polynucleotide encoding the light chain comprises SEQ ID NO: 3. The polynucleotide encoding the $V_H$ chain comprises SEQ ID NOs:5-10. The polynucleotide of SEQ ID NO:1 encodes the intact $V_H$ chain. The polynucleotide encoding the $V_L$ chain comprises SEQ ID NOs:11-16. The polynucleotide of SEQ ID NO:3 encodes the intact $V_L$ chain.

In another aspect, the invention includes an isolated anti-GPC3 antibody or fragment thereof comprising a heavy chain and a light chain, wherein the isolated polypeptide specifically binds to SEQ ID NO:17. SEQ ID NO: 17 corresponds to amino acids 387-407 of GPC3.

In one embodiment, a polynucleotide of the invention encoding anti-glypican heavy and light chain variable regions. The polynucleotide is homologous to polynucleotide sequences encoding the antibodies described herein, wherein the encoded antibodies retain the desired functional properties of the anti-glypican-3 antibodies of the invention.

For example, the invention includes an isolated polynucleotide encoding an antibody, or fragment thereof, comprising a heavy chain variable region and a light chain variable region, wherein: (a) the polynucleotide encoding the heavy chain variable region comprises a polynucleotide sequence, such as SEQ ID NO:1 or a polynucleotide sequence that is at least 75%, 80%, 85%, 90%, 91%, 92%, 93%, 94%, 95%, 96%, 97%, 98% or 99% identical to the polynucleotide sequence of SEQ ID NO:1; (b) the polynucleotide encoding the light chain variable region comprises a polynucleotide sequence, such as SEQ ID NO:3 or a polynucleotide sequence that is at least 75%, 80%, 85%, 90%, 91%, 92%, 93%, 94%, 95%, 96%, 97%, 98% or 99% identical to the polynucleotide sequence of SEQ ID NO:3.

Another aspect of the invention includes an isolated polypeptide for an anti-glypican-3 (GPC3) antibody or fragment thereof comprising a heavy chain and a light chain. The isolated polypeptide of the heavy chain comprises SEQ ID NO: 2 and the isolated polypeptide of the light chain comprises SEQ ID NO: 4. In one embodiment, the polypeptide for the intact $V_H$ chain comprises SEQ ID NO:2. In another embodiment, the polypeptide for the intact $V_L$ chain comprises SEQ ID NO:4.

In one embodiment, an antibody of the invention comprises heavy and light chain variable regions comprising amino acid sequences that are homologous to the amino acid sequences of the antibodies described herein, and wherein the antibodies retain the desired functional properties of the anti-glypican-3 antibodies of the invention.

For example, the invention provides an isolated antibody, or antigen binding portion thereof, comprising a heavy chain variable region and a light chain variable region, wherein: (a) the heavy chain variable region comprises an amino acid sequence that is at least 75%, 80%, 85%, 90%, 91%, 92%, 93%, 94%, 95%, 96%, 97%, 98% or 99% homologous to an amino acid sequence of SEQ ID NO:2; (b) the light chain variable region comprises an amino acid sequence that is at least 75%, 80%, 85%, 90%, 91%, 92%, 93%, 94%, 95%, 96%, 97%, 98% or 99% homologous to an amino acid sequence of SEQ ID NO:4. In one embodiment, the antibody binds to human glypican-3 with an affinity of affinity EC50 ranging from 5.0-110.9 nM.

In one embodiment, the antibody contains heavy chain variable regions having CDRs 1, 2 and 3 including the polynucleotide sequences set forth in SEQ ID NOs:6, 8, and 10.

In one embodiment, the antibody contains light chain variable regions having CDRs 1, 2 and 3 including the polynucleotide sequences set forth in SEQ ID NOs:12, 14, and 16

In certain embodiments, an antibody of the invention comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the antibodies described herein (e.g., 4E5), or conservative modifications thereof, and wherein the antibodies retain the desired functional properties of the anti-glypican-3 antibodies. Accordingly, the invention includes an isolated antibody (e.g., scFv), or antigen binding portion thereof, comprising a heavy chain variable region comprising CDR1, CDR2, and CDR3 sequences and a light chain variable region comprising CDR1, CDR2, and CDR3 sequences, wherein: (a) the heavy chain variable region CDR3 sequence is encoded by a polynucleotide sequence comprising SEQ ID NO:10, and conservative modifications thereof; (b) the light chain variable region CDR3 sequence is encoded by a polynucleotide sequence comprising SEQ ID NO:16, and conservative modifications thereof. In one embodiment, the antibody binds to human glypican-3 with an affinity of affinity EC50 ranging from 5.0-110.9 nM.

In one embodiment, the antibody fragment or antigen binding domain (such as a GPC3 binding domain) can be a Fab fragment, a F(ab')$_2$ fragment, an Fv fragment, and a single chain Fv (scFv). In another embodiment, antibody or fragment thereof is selected from the group consisting of an antigen-binding (Fab), a single-chain variable fragment (scFv), a single-domain antibody, and fragment thereof.

In another embodiment, the invention provides antibodies that bind to the same epitope on human glypican-3 as any of the glypican-3 antibodies of the invention (i.e., antibodies that have the ability to cross-compete for binding to glypican-3 with any of the antibodies of the invention). In yet another embodiment, the reference antibody for cross-competition studies can be one of the antibodies described herein (e.g., 4E5). Such cross-competing antibodies can be identified based on their ability to cross-compete with another antibody in a standard Glypican-3 binding assays. For example, Biacore analysis, ELISA assays or flow cytometry may be used to demonstrate cross-competition with the antibodies of the current invention. The ability of a test antibody to inhibit the binding of, for example, 4E5, to human glypican-3 demonstrates that the test antibody can compete with 4E5 for binding to human glypican-3 and thus binds to the same epitope on human glypican-3 as 4E5.

An antibody of the invention further can be prepared using an antibody having one or more of the VH and/or VL sequences disclosed herein can be used as starting material to engineer a modified antibody, which modified antibody may have altered properties as compared to the starting antibody. An antibody can be engineered by modifying one or more amino acids within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

Human Antibodies

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice.

The chimeric mice are then bred to produce homozygous offspring which express human antibodies. The transgenic mice are immunized in the normal fashion with a selected antigen, e.g., all or a portion of a polypeptide of the invention. Anti-glypican-3 antibodies directed against the human glypican-3 antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For an overview of this technology for producing human antibodies, see, Lonberg and Huszar (Int. Rev. Immunol., 13:65-93 (1995)). For a detailed discussion of this technology for producing human antibodies and human monoclonal antibodies and protocols for producing such antibodies, see, e.g., PCT Publication Nos. WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above. For a specific discussion of transfer of a human germ-line immunoglobulin gene array in germ-line mutant mice that will result in the production of human antibodies upon antigen challenge see, e.g., Jakobovits et al., Proc. Natl. Acad. Sci. USA, 90:2551 (1993); Jakobovits et al., Nature, 362:255-258 (1993); Bruggermann et al., Year in Immunol., 7:33 (1993); and Duchosal et al., Nature, 355:258 (1992).

Human antibodies can also be derived from phage-display libraries (Hoogenboom et al., J. Mol. Biol., 227:381 (1991); Marks et al., J. Mol. Biol., 222:581-597 (1991); Vaughan et al., Nature Biotech., 14:309 (1996)). Phage display technology (McCafferty et al., Nature, 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of unimmunized mice. A repertoire of V genes from unimmunized human donors can be constructed and antibodies to a diverse array of antigens (including self-antigens) can be isolated essentially following the techniques described by Marks et al., J. Mol. Biol., 222:581-597 (1991), or Griffith et al., EMBO J., 12:725-734 (1993). See, also, U.S. Pat. Nos. 5,565,332 and 5,573,905, each of which is incorporated herein by reference in its entirety.

Human antibodies may also be generated by in vitro activated B cells (see, U.S. Pat. Nos. 5,567,610 and 5,229,275, each of which is incorporated herein by reference in its entirety). Human antibodies may also be generated in vitro using hybridoma techniques such as, but not limited to, that described by Roder et al. (Methods Enzymol., 121:140-167 (1986)).

In some instances, a human scFv may also be derived from a yeast display library.

Humanized Antibodies

Alternatively, in some embodiments, a non-human antibody is humanized, where specific sequences or regions of the antibody are modified to increase similarity to an antibody naturally produced in a human. In one embodiment, the antigen binding domain portion is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. No. 6,407,213, U.S. Pat. No. 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, preferably improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some framework (FR) residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

Humanizing variable domains, both light and heavy, antibodies reduces antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993), the contents of which are incorporated herein by reference herein in their entirety).

Antibodies can be humanized with retention of high affinity for the target antigen and other favorable biological properties. According to one aspect of the invention, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

A humanized antibody retains a similar antigenic specificity as the original antibody, i.e., in the present invention, the ability to bind human glypican-3. However, using certain methods of humanization, the affinity and/or specificity of binding of the antibody for human glypican-3 may be increased using methods of "directed evolution," as described by Wu et al., J. Mol. Biol., 294:151 (1999), the contents of which are incorporated herein by reference herein in their entirety.

CAR Composition

The present invention encompasses a recombinant DNA construct comprising sequences of an antibody of the invention that binds specifically to glypican-3, wherein the sequence of the antibody or a fragment thereof is operably linked to the nucleic acid sequence of an intracellular domain. In one aspect, the invention includes an isolated nucleic acid sequence encoding a chimeric antigen receptor (CAR) comprising a glypican-3 (GPC3) binding domain, a transmembrane domain, a costimulatory signaling region, and a CD3 zeta signaling domain.

The intracellular domain or otherwise the cytoplasmic domain comprises, a costimulatory signaling region and/or a zeta chain portion. The costimulatory signaling region refers to a portion of the CAR comprising the intracellular domain of a costimulatory molecule. Costimulatory molecules are cell surface molecules other than antigens receptors or their ligands that are required for an efficient response of lymphocytes to antigen. In one embodiment, the costimulatory signaling domain is any of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

The present invention encompasses a recombinant DNA construct comprising sequences of a CAR, wherein the sequence comprises the nucleic acid sequence of a GPC3 binding domain operably linked to the nucleic acid sequence of an intracellular domain. An exemplary intracellular domain that can be used in the CAR includes but is not limited to the intracellular domain of CD3-zeta, CD28, 4-1BB, and the like. In some instances, the CAR can comprise any combination of CD3-zeta, CD28, 4-1BB, and the like.

Between the extracellular domain and the transmembrane domain of the CAR, or between the cytoplasmic domain and the transmembrane domain of the CAR, a spacer domain may be incorporated. As used herein, the term "spacer domain" generally means any oligo- or polypeptide that functions to link two domains, such as the transmembrane domain to, either the extracellular domain or, the cytoplasmic domain, in the polypeptide chain. A spacer domain may comprise up to 300 amino acids, 10 to 100 amino acids, or 25 to 50 amino acids.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

Antigen Binding Moiety

In one embodiment, the CAR of the invention comprises a target-specific binding element otherwise referred to as an antigen binding moiety. The choice of moiety depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen moiety domain in the CAR of the invention include those associated with viral, bacterial and parasitic infections, autoimmune disease and cancer cells.

In one embodiment, the CAR-mediated T-cell response can be directed to an antigen of interest by way of engineering a desired antigen into the CAR. In the context of the present invention, "tumor antigen" or "hyperproliferative disorder antigen" or "antigen associated with a hyperproliferative disorder" refers to antigens that are common to specific hyperproliferative disorders. In certain aspects, the hyperproliferative disorder antigens of the present invention are derived from, cancers including but not limited to primary or metastatic melanoma, thymoma, lymphoma, sarcoma, lung cancer, liver cancer, non-Hodgkin's lymphoma, Hodgkins lymphoma, leukemias, uterine cancer, cervical cancer, bladder cancer, kidney cancer and adenocarcinomas such as breast cancer, prostate cancer, ovarian cancer, pancreatic cancer, and the like. In one embodiment, the cancer is hepatocellular carcinoma (HCC).

In one embodiment, the tumor antigen of the present invention comprises one or more antigenic cancer epitopes immunologically recognized by tumor infiltrating lymphocytes (TIL) derived from a cancer tumor of a mammal.

In another embodiment, the antigen binding moiety portion of the CAR targets glypican-3, such as human glypican-3. In one embodiment, an isolated nucleic acid sequence encodes the GPC3 binding domain that comprises SEQ ID NO: 1 and SEQ ID NO: 3. In another embodiment, the GPC3 binding domain comprises SEQ ID NO: 2 and SEQ ID NO: 4.

The antigen binding domain comprises an antibody or fragment thereof. The antigen binding domain can be any domain that binds to the antigen including but not limited to monoclonal antibodies, polyclonal antibodies, synthetic antibodies, human antibodies, humanized antibodies, and fragments thereof. In some instances, it is beneficial for the antigen binding domain to be derived from the same species in which the CAR will ultimately be used in. For example, for use in humans, it may be beneficial for the antigen binding domain of the CAR to comprise a human antibody or a fragment thereof.

For in vivo use of antibodies in humans, it may be preferable to use human antibodies. Completely human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO98/16654, WO 96/34096, WO 96/33735, and WO 91/10741; each of which is incorporated herein by reference in its entirety. A human antibody can also be an antibody wherein the heavy and light chains are encoded by a nucleotide sequence derived from one or more sources of human DNA.

Transmembrane Domain

With respect to the transmembrane domain, the CAR can be designed to comprise a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. In some instances, a variety of human hinges can be employed as well including the human Ig (immunoglobulin) hinge.

In one embodiment, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, such as between 2 and 10 amino acids in length may form the linkage between any domain of the CAR. For example, a polypeptide linker may be between the transmembrane domain and the cytoplasmic signaling domain of the CAR. A glycine-serine doublet provides is one example of a suitable linker.

Cytoplasmic Domain

The cytoplasmic domain or otherwise the intracellular signaling domain of the CAR of the invention is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Some examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. In some embodiment, cytoplasmic signaling molecule in the CAR of the invention comprises a cytoplasmic signaling sequence derived from CD3-zeta.

In another embodiment, the cytoplasmic domain of the CAR can be designed to comprise the CD3-zeta signaling domain by itself or combined with any other desired cytoplasmic domain(s) useful in the context of the CAR of the invention. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include, but are not limited to, CD3 zeta, CD3 gamma, CD3 delta, CD3 epsilon, CD86, common FcR gamma, FcR beta (Fc Epsilon Rib), CD79a, CD79b, Fcgamma RIIa, DAP10, DAP12, T cell receptor (TCR), CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, other co-stimulatory molecules described herein, any derivative, variant, or fragment thereof, any synthetic sequence of a co-stimulatory molecule that has the same functional capability, and any combination thereof.

In one embodiment, the cytoplasmic domain is designed to comprise the signaling domain of CD3-zeta and the signaling domain of CD28. In another embodiment, the cytoplasmic domain is designed to comprise the signaling domain of CD3-zeta and the signaling domain of 4-1BB.

Vectors

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., MOLECULAR CLONING: A LABORATORY MANUAL, volumes 1-3 ($3^{rd}$ ed., Cold Spring Harbor Press, N.Y. 2001), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., MOLECULAR CLONING: A LABORATORY MANUAL volumes 1-3 ($3^{rd}$ ed., Cold Spring Harbor Press, N.Y. 2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Sources of T Cells

Prior to expansion and genetic modification, a source of T cells is obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter Cyto- Mate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another embodiment, the time period is 10 to 24 hours. In one embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be selected for or against at culture initiation or at other time points during the process. Additionally, by increasing or decreasing the ratio of anti-CD3 and/or anti-CD28 antibodies on the beads or other surface, subpopulations of T cells can be selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4 T cells express higher levels of CD28 and are more efficiently captured than $CD8^+$ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

In some embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

T cells are activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besançon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one ratio being at least 1:1 particles per T cell. In one embodiment, a ratio of particles to cells of 1:1 or less is used. In one particular embodiment, a particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, such as PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4+) that is greater than the cytotoxic or suppressor T cell population ($T_C$, CD8+). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application

In one aspect, the invention includes a pharmaceutical composition comprising an effective amount of the isolated polynucleotide encoding the anti-GPC3 antibody described herein. In another embodiment, the invention includes a pharmaceutical composition comprising an effective amount of the isolated polypeptide described herein. In one embodiment, the pharmaceutical composition further comprises a pharmaceutically or physiologically acceptable carrier, diluent or excipient.

In another aspect, the invention includes a pharmaceutical composition comprising an effective amount of the isolated polynucleotide encoding the CAR described herein. In another embodiment, the invention includes a pharmaceutical composition comprising an effective amount of the isolated CAR described herein. In one embodiment, the pharmaceutical composition further comprises a pharmaceutically or physiologically acceptable carrier, diluent or excipient.

In another aspect, the invention pertains to a method of imaging or visualizing a sample taken from a normal or malignant tissue, such as liver tissue, comprising contacting the sample with a labeled anti-GPC3 antibody or fragment thereof. In another embodiment, a method includes diagnosing a condition associated with expression of GPC3 in a cell. In yet another embodiment, the invention includes diagnosing, prognosing, or determining risk of liver cancer in a subject.

In yet another aspect, the invention includes inhibiting growth of a GPC3-expressing tumor cell comprising contacting the tumor cell with at least one antibody or a fragment thereof of the invention such that growth of the tumor cell is inhibited. The tumor cell is contacted with the anti-GPC3 antibody or a fragment thereof, which is described elsewhere herein.

The invention includes contacting the sample, tumor cell, or cell with the anti-GPC3 antibody or fragment thereof as described elsewhere herein. The method also includes detecting GPC3 expression, wherein the expression of GPC3 indicates a likelihood of a condition, such as liver cancer, associated with the expression of GPC3.

In another aspect, the invention pertains to a method of treating cancer in a subject. The method comprises administering to the subject an antibody or a fragment of the invention or an anti-GPC3 CART cell of the present invention such that the cancer is treated in the subject. In one embodiment, the invention includes providing an anti-tumor immunity in a subject comprising administering to the subject an effective amount of a genetically modified cell comprising an isolated nucleic acid sequence encoding a chimeric antigen receptor (CAR) that comprises a glypican-3 (GPC3) binding domain and a CD3 zeta signaling domain, wherein the GPC3 binding domain comprises a heavy chain comprising SEQ ID NO: 2 and a light chain comprising SEQ ID NO: 4. The modified cell may include a T cell, such as an autologous T cell.

Some cancers for treatment are hepatocellular carcinomas, pancreatic cancers, ovarian cancers, stomach cancers, lung cancers and endometrial cancers. In still other embodiments, the cancer to be treated is selected from the group consisting of hepatocellular carcinomas, papillary serous ovarian adenocarcinomas, clear cell ovarian carcinomas, mixed Mullerian ovarian carcinomas, endometroid mucinous ovarian carcinomas, pancreatic adenocarcinomas, ductal pancreatic adenocarcinomas, uterine serous carcinomas, lung adenocarcinomas, extrahepatic bile duct carcinomas, gastric adenocarcinomas, esophageal adenocarcinomas, colorectal adenocarcinomas and breast adenocarcinomas.

In another embodiment, the invention includes treating a subject having a disease, disorder or condition associated with dysregulated expression of glypican-3, the method comprising administering to the subject an effective amount of a genetically modified cell comprising an isolated nucleic acid sequence encoding a chimeric antigen receptor (CAR) that comprises a GPC3 binding domain and a CD3 zeta signaling domain, wherein the GPC3 binding domain comprises SEQ ID NO: 2 and SEQ ID NO: 4. The disease, disorder or condition associated with dysregulated expression of GPC3 may include liver cancer, pancreatic cancer, ovarian cancer, stomach cancer, lung cancer, endometrial cancer, hepatocellular carcinoma, and any combination thereof.

The present invention includes a type of cellular therapy where T cells are genetically modified with an isolated nucleic acid sequence encoding the chimeric antigen receptor (CAR) or to express the CAR. The CAR T cell is infused to a recipient in need thereof. The infused cell is able to kill tumor cells in the recipient. Unlike antibody therapies, CAR-modified T cells are able to replicate in vivo resulting in long-term persistence that can lead to sustained tumor control. In various embodiments, the T cells administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the T cell to the patient.

Without wishing to be bound by any particular theory, the anti-tumor immunity response elicited by the CAR-modified T cells may be an active or a passive immune response. In another embodiment, the fully-human CAR transduced T cells exhibit specific proinflammatory cytokine secretion and potent cytolytic activity in response to human cancer cells expressing the GPC3, resist soluble GPC3 inhibition, mediate bystander killing and mediate regression of an established human tumor. For example, antigen-less tumor cells within a heterogeneous field of GPC3-expressing tumor may be susceptible to indirect destruction by GPC3-redirected T cells that has previously reacted against adjacent antigen-positive cancer cells.

The fully-human CAR-modified T cells of the invention may be a type of vaccine for ex vivo immunization and/or in vivo therapy in a mammal. In one embodiment, the mammal is a human.

With respect to ex vivo immunization, at least one of the following occurs in vitro prior to administering the cell into a mammal: i) expansion of the cells, ii) introducing a nucleic acid encoding a CAR to the cells or iii) cryopreservation of the cells.

Ex vivo procedures are well known in the art and are discussed more fully below. Briefly, cells are isolated from a mammal (such as a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified T cells of the invention are used in the treatment of diseases, disorders and conditions associated with dysregulated expression of GPC3. In certain embodiments, the cells of the invention are used in the treatment of patients at risk for developing diseases, disorders and conditions associated with dysregulated expression of GPC3. Thus, the present invention provides methods for the treatment or prevention of diseases, disorders and conditions associated with dysregulated expression of GPC3 comprising administering to a subject in need thereof, a therapeutically effective amount of the CAR-modified T cells of the invention.

The CAR-modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount," "an anti-tumor effective amount," "an tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, such as $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol, may select out certain populations of T cells.

The administration of the subject compositions may be carried out in any convenient manner, including by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAM-PATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAM-PATH, for example, will generally be in the range 1 to about 100 mg for an adult patient, usually administered daily for a period between 1 and 30 days. In one embodiment, the daily dose is 1 to 10 mg per day although in some instances larger doses of up to 40 mg per day may be used (described in U.S. Pat. No. 6,120,766).

Diagnostic Method

In another aspect, the present invention provides a method of diagnosing a disease such as cancer by detecting GPC3 protein in a test sample with the use of the antibody of the present invention.

The detection used herein includes quantitative detection and non-quantitative detection. The non-quantitative detection include, for example, determination of merely whether or not GPC3 protein is present, determination of whether or not a specific amount or more of GPC3 protein is present, determination for comparison of the amount of GPC3 protein with that of another sample (e.g., a control sample). The quantitative detection includes determination of the concentration of GPC3 protein, determination of the amount of GPC3 protein.

The test sample is not particularly limited as long as it is a sample that may contain GPC3 protein, however, a sample includes those collected from the body of a living organism such as a mammal, and a human. Specific examples of the test sample may include, for example, blood, interstitial fluid, plasma, extravascular fluid, cerebral fluid, joint fluid, pleural fluid, serum, lymph fluid, saliva, such as blood, serum and plasma. In addition, a sample obtained from the test sample such as culture solution of cells collected from the body of the living organism is also included in the test sample of the present invention.

The cancer to be diagnosed is not particularly limited, and specific examples may include liver cancer, pancreatic cancer, lung cancer, colon cancer, mammary cancer, prostate cancer, leukemia and lymphoma, such as liver cancer. GPC3 to be detected is not particularly limited, and may be either full-length GPC3 or a fragment thereof. In the case where a fragment of GPC3 is detected, it may be either the N-terminal fragment or the C-terminal fragment.

The method of detecting GPC3 protein contained in a test sample is not particularly limited, however, detection is performed by an immunological method with the use of an anti-GPC3 antibody. Examples of the immunological method include, for example, a radioimmunoassay, an enzyme immunoassay, a fluorescence immunoassay, a luminescence immunoassay, immunoprecipitation, a turbidimetric immunoassay. In one embodiment, the immunological method is an enzyme immunoassay, or an enzyme-linked immunosorbent assay (ELISA) (e.g., a sandwich ELISA). The above-mentioned immunological method such as an ELISA can be carried out by a method known to those skilled in the art.

A general detection method with the use of an anti-GPC3 antibody comprises immobilizing an anti-GPC3 antibody on a support, adding a test sample thereto, incubating the support to allow the anti-GPC3 antibody and GPC3 protein to bind to each other, washing the support, and detecting the GPC3 protein binding to the support via the anti-GPC3 antibody to detect GPC3 protein in a test sample.

The binding between the anti-GPC3 antibody and the GPC3 protein is generally carried out in a buffer. Buffers used in the invention include, for example, a phosphate buffer, a Tris buffer. Incubation is carried out under the conditions generally employed, for example, at 4° C. to room temperature for 1 hour to 24 hours. The washing after incubation can be carried out by any method as long as it does not inhibit the binding between the GPC3 protein and the anti-GPC3 antibody, using for example a buffer containing a surfactant such as Tween 20.

In the method of detecting GPC3 protein of the present invention, a control sample may be provided in addition to a test sample to be tested for GPC3 protein. The control samples include a negative control sample that does not contain GPC3 protein and a positive control sample that contains GPC3 protein. In this case, it is possible to detect GPC3 protein in the test sample by comparing the result obtained with the negative control sample that does not contain GPC3 protein with the result obtained with the positive control sample that contains GPC3 protein. It is also possible to quantitatively detect GPC3 protein contained in the test sample by obtaining the detection results of the control samples and the test sample as numerical values, and comparing these numerical values.

In one embodiment, a method of detecting GPC3 protein binding to the support via an anti-GPC3 antibody includes using an anti-GPC3 antibody labeled with a detectable label. For example, GPC3 protein may be detected by contacting the test sample with an anti-GPC3 antibody immobilized on the support, washing the support, and then detecting GPC3 with the use of the labeled antibody that specifically binds to GPC3 protein.

The labeling of an anti-GPC3 antibody can be carried out by a generally known method. Examples of the detectable label known to those skilled in the art include a fluorescent dye, an enzyme, a coenzyme, a chemiluminescent substance or a radioactive substance. Specific examples may include radioisotopes ($^{32}P$, $^{14}C$, $^{125}I$, $^{3}H$, $^{131}I$ and the like), fluorescein, rhodamine, dansyl chloride, umbelliferone, luciferase, peroxidase, alkaline phosphatase, beta-galactosidase, beta-glucosidase, horseradish peroxidase, glucoamylase, lysozyme, saccharide oxidase, microperoxidase, biotin and the like. In the case where biotin is used as a detectable label, a biotin-labeled antibody is added, and then avidin conjugated to an enzyme such as alkaline phosphatase is further added.

Specifically, a solution containing an anti-GPC3 antibody is added to a support such as a plate to allow the anti-GPC3 antibody to be immobilized. After washing, the plate is blocked with, for example, BSA in order to prevent the nonspecific binding of a protein. The plate is washed again, and then the test sample is added to the plate. After being incubated, the plate is washed, and then the labeled anti-GPC3 antibody is added. After being incubated appropriately, the plate is washed, and then the labeled anti-GPC3 antibody remaining on the plate is detected. The detection of the protein can be carried out by a method known to those skilled in the art. For example, in the case where the antibody is labeled with a radioactive substance, the protein may be detected by liquid scintillation or the RIA method. In the case where the antibody is labeled with an enzyme, the protein may be detected by adding a substrate and detecting an enzymatic change of the substrate such as color development with an absorbance reader. In the case where the antibody is labeled with a fluorescent substance, the protein may be detected with the use of a fluorometer.

In one embodiment, the method of detecting GPC3 protein of the present invention is a method using an anti-GPC3 antibody labeled with biotin and avidin. Specifically, a solution containing an anti-GPC3 antibody is added to a support such as a plate to allow the anti-GPC3 antibody to be immobilized thereon. After washing, the plate is blocked with, for example, BSA in order to prevent the nonspecific binding of a protein. The plate is washed again, and then the test sample is added to the plate. After being incubated, the plate is washed, and then the biotin-labeled anti-GPC3 antibody is added. After being incubated appropriately, the plate is washed, and then avidin conjugated to an enzyme such as alkaline phosphatase or peroxidase is added. After being incubated, the plate is washed, and then a substrate of the enzyme conjugated to avidin is added. Then, GPC3 protein is detected by means of the enzymatic change of the substrate as an indicator.

In another embodiment, the method of detecting GPC3 protein of the present invention includes a method using a primary antibody that specifically binds to GPC3 protein and a secondary antibody that specifically binds to the primary antibody. For example, the test sample is brought into contact with an anti-GPC3 antibody immobilized on the support, the support is incubated and washed, and the bound GPC3 protein after washing is detected with a primary anti-GPC3 antibody and a secondary antibody that specifically binds to the primary antibody. In this case, the secondary antibody is labeled with a detectable label.

Specifically, a solution containing an anti-GPC3 antibody is added to a support such as a plate to allow the anti-GPC3 antibody to be immobilized thereon. After washing, the plate is blocked with, for example, BSA in order to prevent the nonspecific binding of a protein. The plate is washed again, and then the test sample is added to the plate. After being incubated, the plate is washed, and then a primary anti-GPC3 antibody is added. After being incubated appropriately, the plate is washed, and then a secondary antibody that specifically binds to the primary antibody is added. After being incubated appropriately, the plate is washed, and then the secondary antibody remaining on the plate is detected. The detection of the secondary antibody can be carried out by the above-mentioned method.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods employed in the following experiments are now described.

4E5 DNA was cloned into a yeast vector, BCCP, and transformed into YP10 yeast cells. 4E5 was secreted as a fusion protein and purified by nickel-HIS beads. 4E5's $EC_{50}$ was assayed by ELISA using against a GPC3-GST fusion protein as an antigen. Estimates of $EC_{50}$ were 43.1 nM at antigen concentration of 1 µg/ml and 52.0 nM at antigen concentration of 0.5 µg/ml.

The ability of 4E5 scFv-Fc to bind antigen was determined by FACS. 4E5 DNA was cloned into pFUSE vector to produce murine IgG2. The construct was transformed into 293T cells and the cells were cultured in serum-free medium. Supernatant was collected and concentrated to about 600 µl to about 6 ml. The supernatant, containing the secreted 4E5 antibody, was incubated with target cells (293T, K562, HepG2 and Huh7 cells). Cells were then stained with anti-mouse APC as a secondary antibody.

scFvs were identified using a yeast display library including one novel scFv. The polynucleotide encoding the novel scFv was incorporated into a lentiviral vector along with a sequence encoding a CD8alpha hinge, an intracellular signaling domain of 4-1BB and CD3zeta, and a nonsignaling control with a truncated CD3zeta (scFv-Dz) was constructed. Human T cells were transduced and expanded with anti-CD3/CD28 beads. Transduction efficiency was confirmed by anti-Fab-FITC staining Cytotoxicity against HepG2 (hGPC3+), HCE4 (hGPC3+), Hepal-6 (mGPC3+), 293T (hGPC3−), K562.meso (hGPC3−) was assessed by Cr51 release assay and cytokine response by Th1/Th2 cytokine bead array.

A murine Fc fusion protein with 4E5 scFv domain was constructed and expressed. Briefly, 4E5 DNA was cloned into pFUSE vector (murine IgG2). The 4E5-Fc fusion construct was transformed into 293T cells and cultured in serum-free medium.

Figure 7:
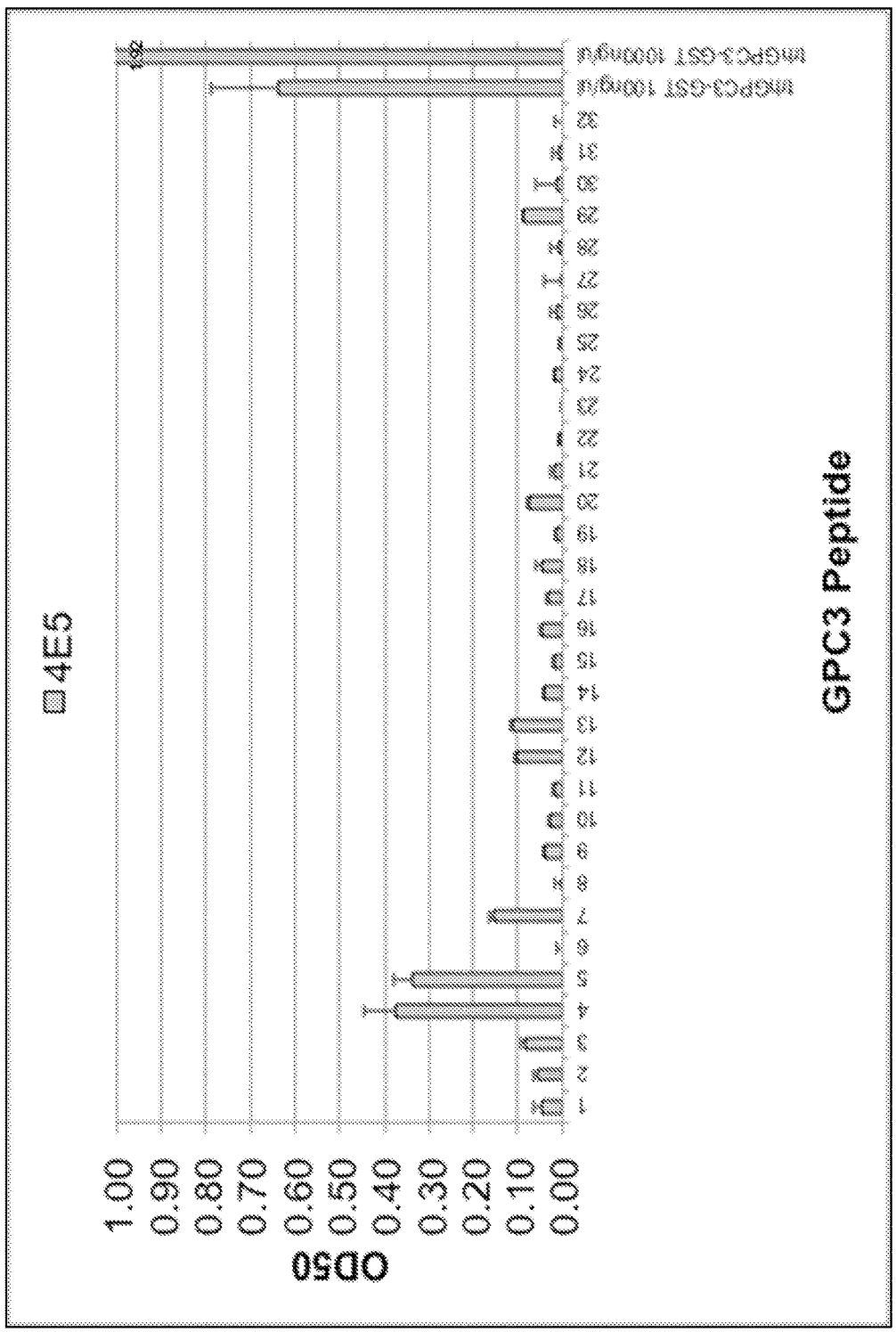
FIG. 7 is a graph showing a 25-mer peptide binding ELISA for 4E5 specificity.

Using the 4E5-Fc fusion protein, an ELISA assay was performed to test binding to 25 mer overlapping peptides from human GPC3. Briefly, 25 mer peptides for the C-terminal 358 aa overlapping by 20 mer were commercially synthesized. These peptides and recombinant whole GPC3 were bound to ELISA plates in duplicate, then 4E5-Fc fusion protein was incubated in each well. After washing, HRP-anti-murine Fc antibody was used to detect specific binding. As shown in FIG. 7, the 4E5-Fc appeared to bind to peptides #4-5, corresponding to the following sequence: RRRELI-QKLKSFISFYSALPG ($GPC3_{387-407}$) (SEQ ID NO:17). Of note, this region is highly homologous across mammalian species with only 1 aa residue change between human and non-human sequences.

For chromium release assays, $2 \times 10^5$ target cells were chromated and co-cultured with 4E5-BBz (active 4-1BB and CD3z signaling domain) or 4E5-DZ (non-signaling) at effector:target ratios of 30:1, 10:1, 3:1, 1:1, 0.3:1, 1:0 for 6 hours.

5×10⁶ 4E5-BBz or 4E5-dZ transduced T-cells were injected by tail vein into 6 non-tumor-bearing C57B1/6J mice. Mice were monitored for toxicity (clinical observation, weight, grooming) for 8 days and then sacrificed. The following tissues were harvested to histological evaluation for injury in brain, heart, spleen, liver, kidney, bone marrow and skin. Tissues were reviewed by the Comparative Pathology Core at the University of Pennsylvania School of Veterinary Medicine and no tissue injury was identified in BBz-treated animals. Flow cytometry detecting eGFP (selection marker in CAR-T transduced cells) and goat anti-Fab (to detect scFv) showed persistence of CAR-T in liver, blood, bone marrow and spleen as shown. CAR-T cells in tissues by immunofluorescence staining was confirmed.

In vivo efficacy experiment 1. 5M Hepa1-6 cells (murine GPC3+ liver cancer cell line) in matrigel were injected subcutaneously into the anterior abdominal wall on one side and 3M were injected into the contralateral side of 6 C57B1/6J mice. 5×10⁶ 4E5 CAR-T transduced cells were preactivated 1-2 days after electroporation using the PiggyBac transposon system, cocultured with mitomycin C-treated murine splenocytes as feeder cells, and injected 3 times. Tumor volume was measured by ultrasound. No clear impact of CAR-T cells on tumor growth was seen. However, tumor sizes were <50 mm³ and transduction efficiency was not clearly defined at the outset of the experiment.

Figure 11:
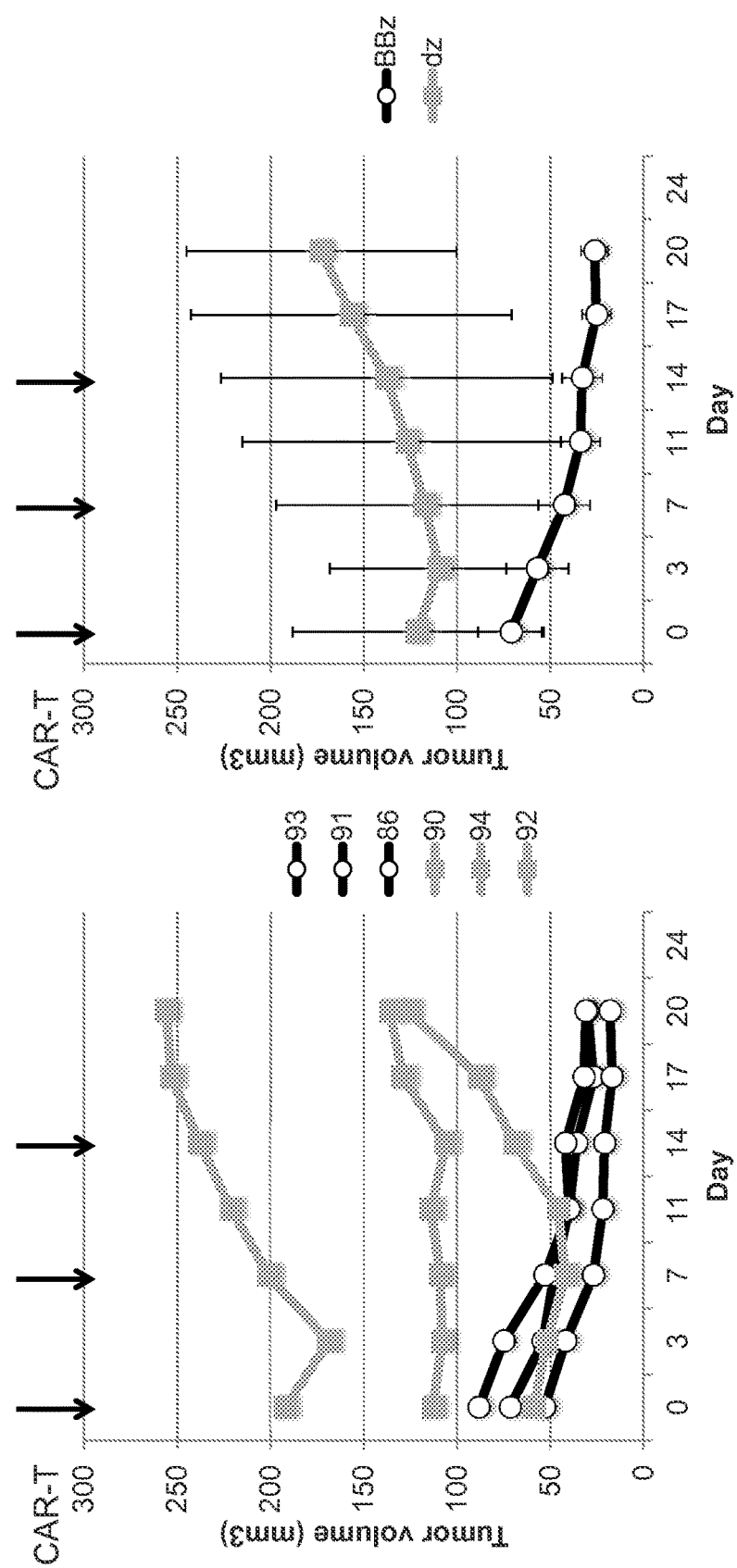
FIG. 11 is a panel of graphs showing tumor volume control as measured by calipers after injection of 4E5 CAR-T cells in immunocompetent mice.

In vivo efficacy experiment 2. The experiment was repeated with 6 mice, injecting 10M Hepa1-6 cells into the right flank, waiting until tumor sizes reached 50 mm³. 5×10⁶ 4E5 CAR-T transduced cells, preactivated 1-2 days after electroporation using PiggyBac transposon system, cocultured with mitomycin C-treated murine splenocytes as feeder cells, and injected 3 times. Tumor volume was measured by calipers (½×L×W×W) every 3 days. 4E5-dz CAR-T (non-signaling) were used as negative control. As shown in FIG. 11, treated tumors regressed, while control tumors slowly progressed.

$V_H$ of 4E5
SEQ ID NO: 1
caggttcaactgcagcagtctggggctgagctggtgaggcctgggcttc agtgaagctgtcctgcaaggcttcgggctacacatttaatgactatgaaa tgcactgggtgaagcagacacctgtgcatggcctaaaatggattggagct cttgagcctaaaactggtgatactgcctacagtcagaagttcaagggcaa ggccacactgactgcagacaaatcctccagcacagcctacatggagctcc gcagcctgacatctgaggactctgccgtctattactgtaccagctgctac tactatacttactcgggccaagggactctggtcactgtctctgca $V_H$ of 4E5
SEQ ID NO: 2
QVQLQQSGAELVRPGASVKLSCKASGYTFNDYEMHWVKQTPVHGLKWIGA

LEPKTGDTAYSQKFKGKATLTADKSSSTAYMELRSLTSEDSAVYYCTSCY

YYTYSGQGTLVTVSA $V_L$ of 4E5
SEQ ID NO: 3
gatgttgtgatgacccaaactccactctccctgcctgtcagtcttggaga tcaagcctccatctcttgcagatctagtcagagccttgtacacagtaatg gaaacacctatttacattggtacctgcagaagccaggccagtctccaaag ctcctgatctacaaagtttccaaccgattttctggggtcccagacaggtt cagtggcagtggatcagggacagatttcacactcaagatcagcagagtgg aggctgaggatctgggagtttatttctgctctcaaaatacacctgttcct cctaagttcggatcggggaccaagctggaaataaaa $V_L$ of 4E5
SEQ ID NO: 4
DVVMTQTPLSLPVSLGDQASISCRSSQSLVHSNGNTYLHWYLQKPGQSPK

LLIYKVSNRFSGVPDRFSGSGSGTDFTLKISRVEAEDLGVYFCSQNTPVP

PKFGSGTKLEIK

FR1 domain of the $V_H$ of 4E5
SEQ ID NO: 5
caggttcaactgcagcagtctggggctgagctggtgaggcctgggcttc agtgaagctgtcctgcaaggcttcg CDR1 domain of the $V_H$ of 4E5
SEQ ID NO: 6
ggctacacatttaatgactatgaa FR2 domain of the $V_H$ of 4E5
SEQ ID NO: 7
atgcactgggtgaagcagacacctgtgcatggcctaaaatggattggagc
t CDR2 domain of the $V_H$ of 4E5
SEQ ID NO: 8
cttgagcctaaaactggtgatact FR3 domain of the $V_H$ of 4E5
SEQ ID NO: 9
gcctacagtcagaagttcaagggcaaggccacactgactgcagacaaatc ctccagcacagcctacatggagctccgcagcctgacatctgaggactctg ccgtctattactgt CDR3 domain of the $V_H$ of 4E5
SEQ ID NO: 10
accagctgctactactatacttactcgggccaagggactctggtcactgt ctct FR1 domain of the $V_L$ of 4E5
SEQ ID NO: 11
gatgttgtgatgacccaaactccactctccctgcctgtcagtcttggaga tcaagcctccatctcttgcagatctagt CDR1 domain of the $V_L$ of 4E5
SEQ ID NO: 12
cagagccttgtacacagtaatggaaacacctatt FR2 domain of the $V_L$ of 4E5
SEQ ID NO: 13
ttacattggtacctgcagaagccaggccagtctccaaagctcctgatcta
c CDR2 domain of the $V_L$ of 4E5
SEQ ID NO: 14
aaagtttcc FR3 domain of the $V_L$ of 4E5
SEQ ID NO: 15
aaccgattttctggggtcccagacaggttcagtggcagtggatcagggac agatttcacactcaagatcagcagagtggaggctgaggatctgggagttt atttctgc -continued CDR3 domain of the $V_L$ of 4E5

SEQ ID NO: 16 tctcaaaatacacctgttcctcctaagttcggatcggggaccaagctg

The results of the experiments are now described.

Example 1: Characterization of GPC3

Figure 2:
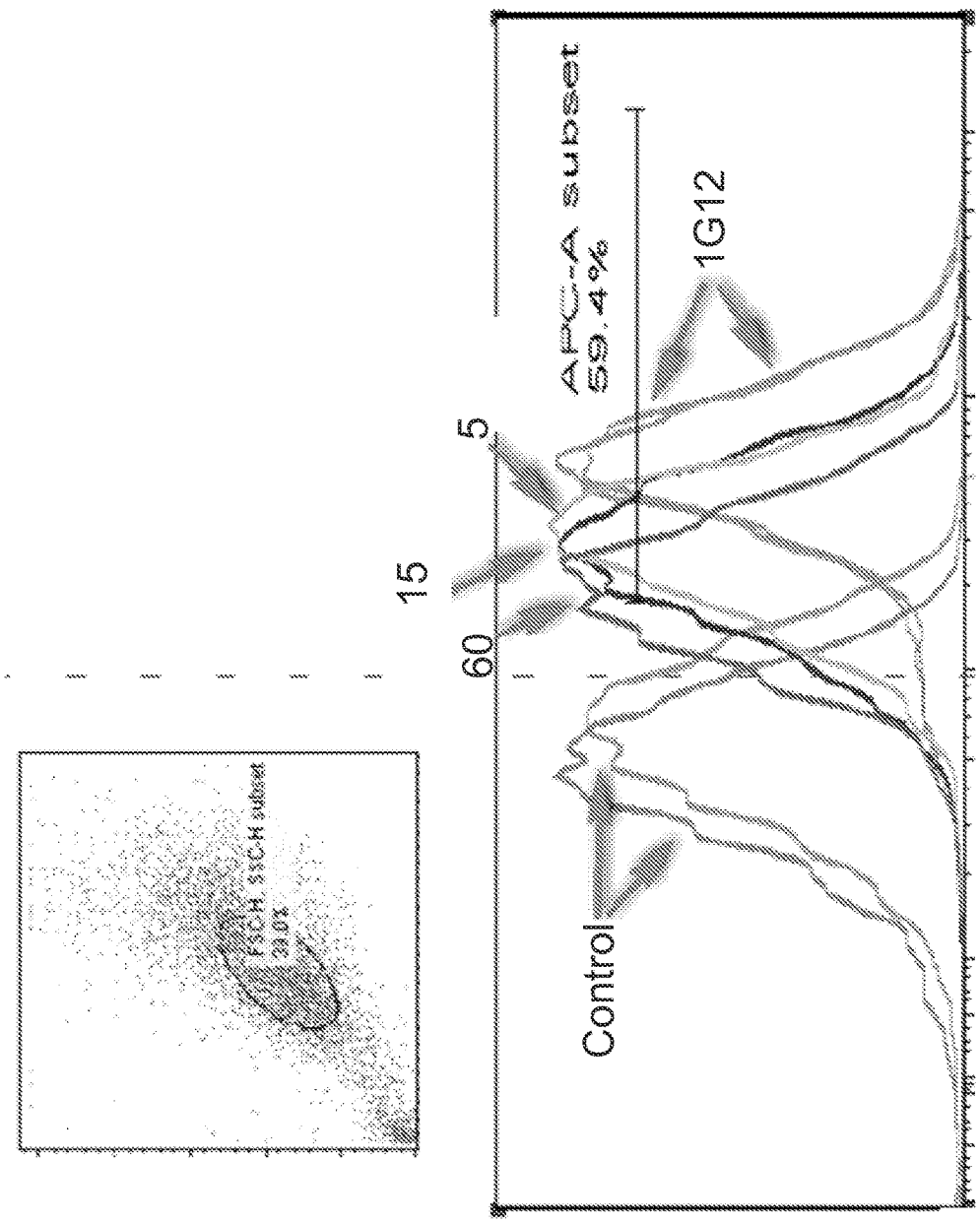
FIG. 2 is a panel of images showing anti-glypican-3 antibody (4E5) bound to glypican-3 positive cells, HepG2. 1G12, GPC3-specific IgG1 antibody, was used as a positive control.

FIGS. 1 and 2 show a panel of images demonstrating anti-glypican-3 antibody (4E5) bound to glypican-3 positive cells, Huh7 and HepG2. GPC3-specific IgG1 antibody, was used as a positive control.

Figure 3:
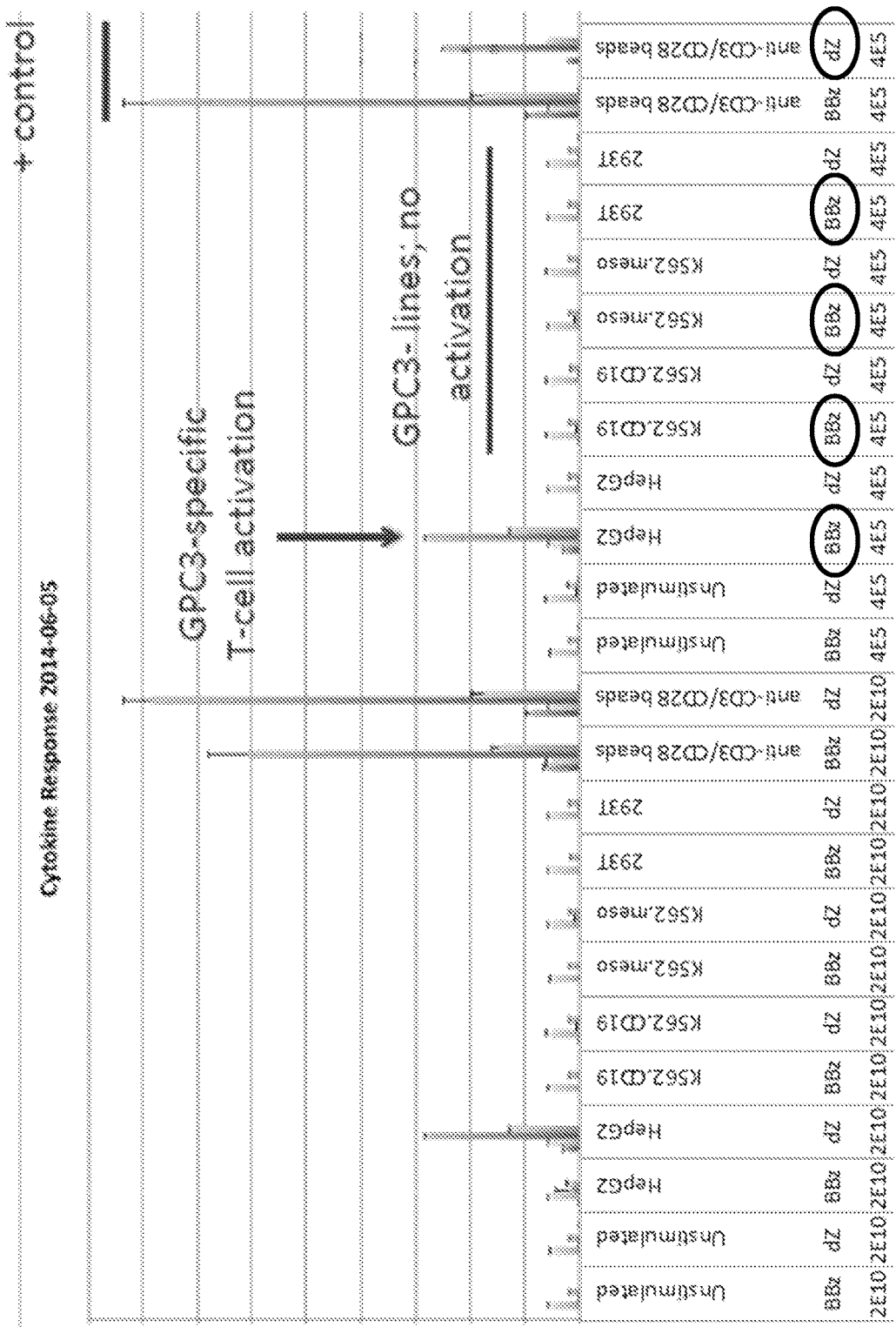
FIG. 3 is a graph showing cytokine production of 4E5-CAR constructs. $2 \times 10^5$ target cells were co-cultured with 4E5-BBz (active 4-1BB and CD3zeta signaling domain) or 4E5-deltaZ (non-signaling) at 1:1 effctor:target cell ratio. Cytokine production was measured with Th1/Th2 Cytokine Bead Array (BD, Rutherford, N.J.).

FIG. 3 is a graph showing cytokine production of 4E5-CAR constructs as a measure of T cell activation. $2 \times 10^5$ target cells were co-cultured with 4E5-BBz (active 4-1BB and CD3zeta signaling domain) or 4E5-deltaZ (non-signaling) at 1:1 effctor:target cell ratio. Cytokine production was measured with Th1/Th2 Cytokine Bead Array (BD, Rutherford, N.J.).

In vivo cytolysis of GPC3-specific 3E11-CAR T cells was determined. Five scFvs candidates (3E11 [Kd 11 nM], 2E10 [Kd 5 nM], 3D8 [Kd 105.5 nM], 4G5 [Kd 38.8 nM], 4E5 [Kd unknown]) were tested. Transduction efficiency ranged from 35-75%. CAR-T cell cytolysis at an Effector:target cell ratio of 10:1 are shown in Table 1. 2D10, 3E11 and 4E5 GPC3-specific CART cells showed strong in vitro cytolysis and specificity. 4E5 cross-reacts with both murine and human GPC3.

TABLE 1

CAR-T cytolysis of scFv candidates.

| scFv | Kd (nM) | HepG2 | HCE4 | Hepa1-6 | 293T | K562meso |
|------|---------|-------|------|---------|------|----------|
| 2D10 | 5.0     | 20%   | 13%  | Neg     | Neg  | Neg      |
| 3E11 | 12.0    | 20%   | 16%  | Neg     | Neg  | Neg      |
| 3D8  | 105.5   | 50%   | Neg  | Neg     | Neg  |          |
| 4G5  | 38.8    | 3%    | Neg  | Neg     | Neg  |          |
| 4E5  | Unknown | 49%   | 21%  | 42%     | Neg  | Neg      |
| SS1  | Unknown |       |      |         | Neg  | 95%      |

Figure 4:
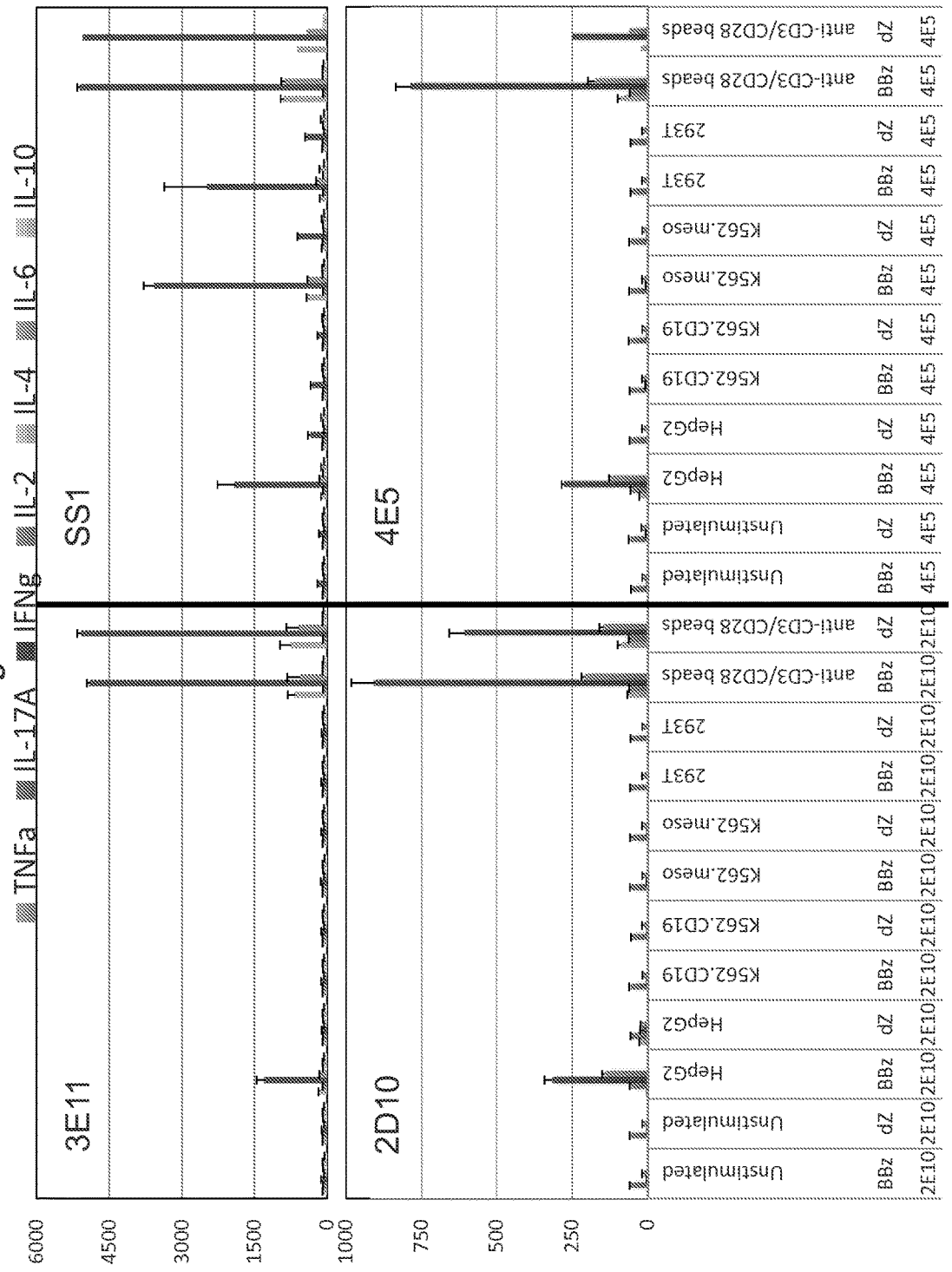
FIG. 4 is a panel of graphs showing in vitro cytokine production of GPC3-specific CAR T cells.

FIG. 4 is a panel of graphs showing in vitro cytokine production of GPC3-specific CAR T cells. In this experiment $5 \times 10^4$ human T-cells were transduced with either the active (BBz) or inactive (delta-z) form of four different CAR constructs (3E11, 2D10, 4E5-GPC3 specific; SS1—mesothelin specific provided by Michael Milone). The T cells were cocultured for 6 hours at 1:1 ratio with no target cells, HepG2 (human liver cancer), K562.CD19 (erythroblast cell line stably expressing CD19), K562.meso (erythroblast cell line stably expressing mesothelin), 293T HEK (human kidney epithelial) or anti-CD3/CD28 beads. Cytokine production was measured by BD T1/T2 cytokine bead array. GPC3 CARs showed specific cytokine production of TNF-alpha, IFN-gamma and IL-2 only with GPC3-expressing HepG2 cell lines.

Figure 5:
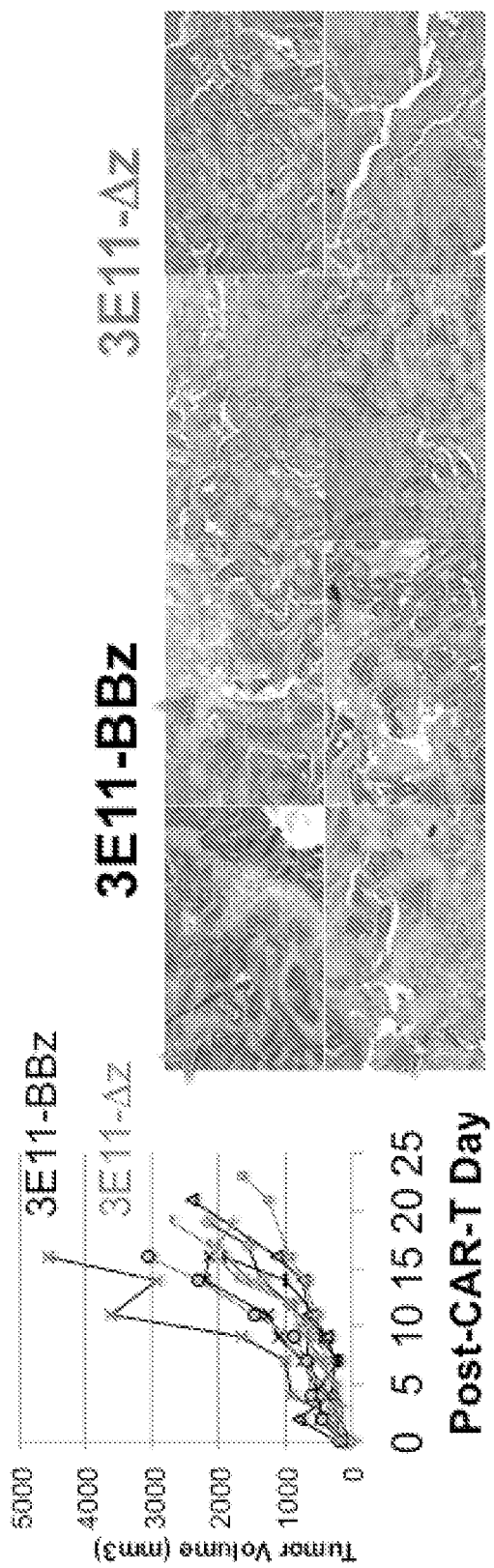
FIG. 5 is a panel of images showing the in vivo cytolysis of GPC3-specific 3E11-CAR T cells.

FIG. 5 shows that one million HepG2 cells were injected in matrigel into the flank of NOD/SCID/IL-2gamma−/− mice. $15 \times 10^6$ transduced T cells were injected on day 12-14 intratumorally with 3E11-BBz (n=4) or 3E11-delta.z (n=4). Tumors ranged in size from 50-100 mm³. No improvement in tumor volume was identified. However, 3E11-BBz tumors showed broad areas of necrosis linked by T cells, whereas 3E11-Δz had quiescent T cells in the needle tracks otherwise normal growth of HepG2 tumor cells.

Figure 6:
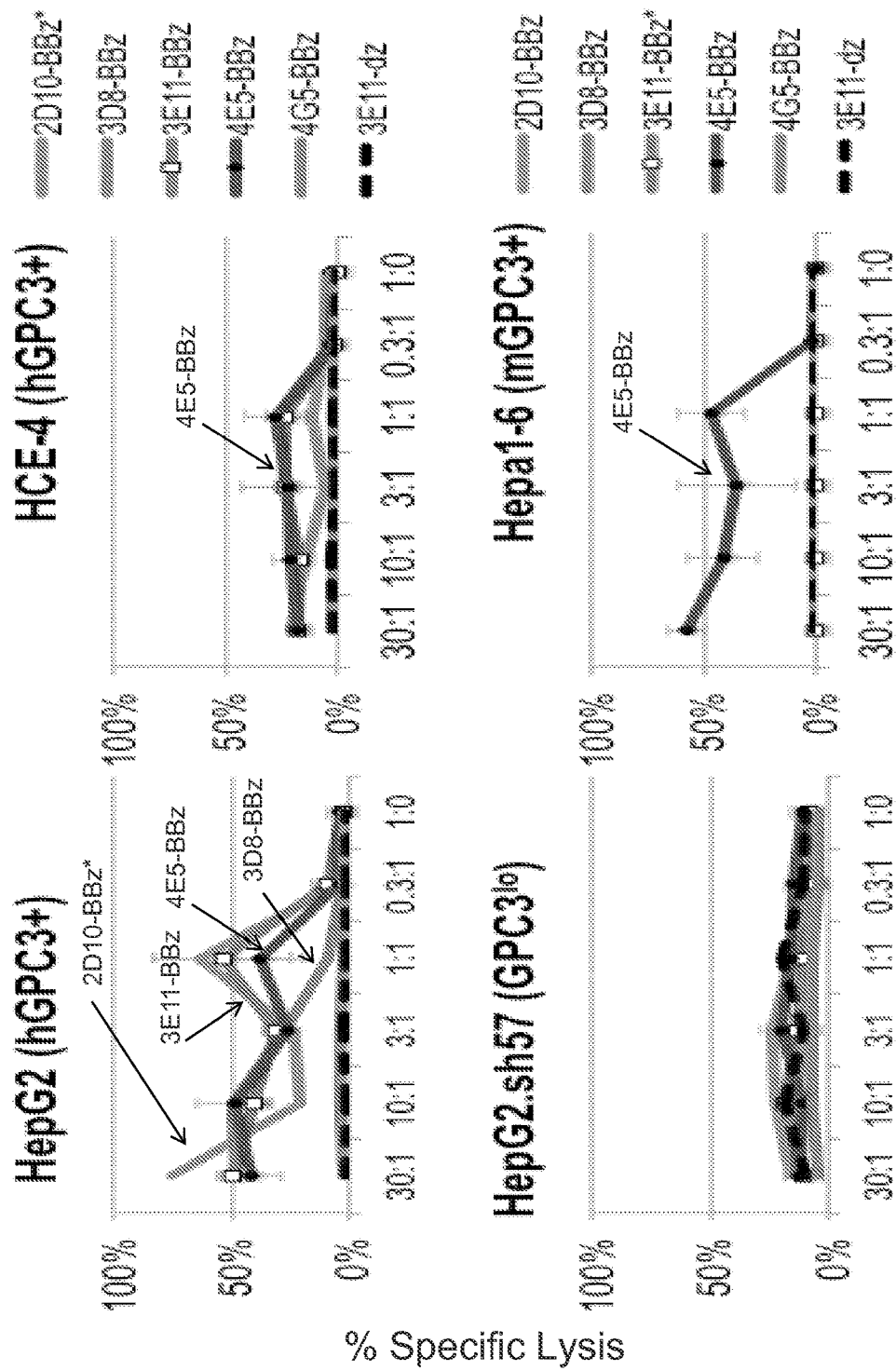
FIG. 6 is a panel of graphs showing the in vitro cytolytic capacity of glypican-3 (GPC3) specific chimeric antigen receptor (CAR) T cells.

FIG. 6 is a panel of graphs showing the in vitro cytolytic capacity of glypican-3 (GPC3) specific chimeric antigen receptor (CAR) T cells.

Example 2: Construction of scFv Fc Fusion Protein

A murine Fc fusion protein with 4E5 scFv domain was constructed and expressed. Briefly, 4E5 DNA was cloned into pFUSE vector (murine IgG2), transformed into 293T cells and cultured in serum-free medium. Supernatant was concentrated 10-fold and incubated with several cell lines (293T, K562, HepG2 and Huh7). 4E5 antibody was detected using an anti-mouse APC secondary antibody. As shown for Huh7 (FIG. 3), the 4E5-Fc fusion protein specifically binds to both human GPC3+ (Huh7, HepG2) and murine GPC3+ (Hepal-6) cell lines by flow cytometric assay.

Example 3: Determination of 4E5 Epitope

Using the 4E5-Fc fusion protein, an ELISA assay was performed to test binding of the antibody to different 25-mer overlapping peptides from human GPC3. As shown in FIG. 7, the 4E5-Fc bound to peptides #4-5, corresponding to the following sequence: RRRELIQKLKSFISFYSALPG ($GPC3_{387-407}$) (SEQ ID NO:17). Of note, this region is highly homologous across mammalian species with only 1 aa residue change between human and non-human sequences.

Example 4: In Vitro and In Vivo Activity

Figure 8:
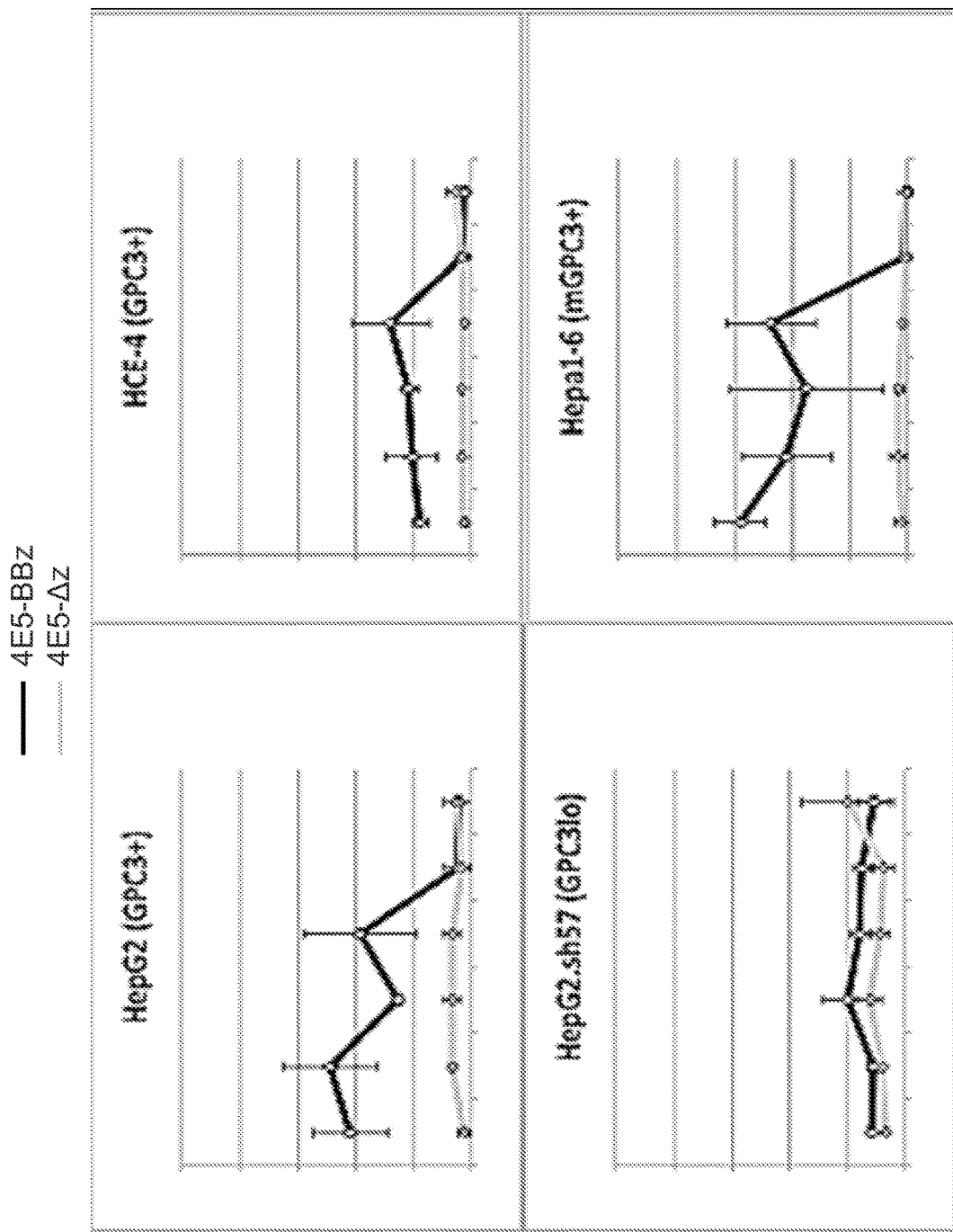
FIG. 8 is a panel of graphs showing a chromium release assay of cytolysis of 4E5 CAR constructs. $2 \times 10^5$ cells were co-cultured with 4E5 BBz (active 4-1BB and CD3z signaling domain) or 4E5-DZ (non-signaling domain) at 1:1 effector:target ratios.

4E5-BBz further demonstrated specific lysis of human GPC3+ and murine GPC3+ tumor cell lines in vitro (FIGS. 3 and 8).

Figure 9:
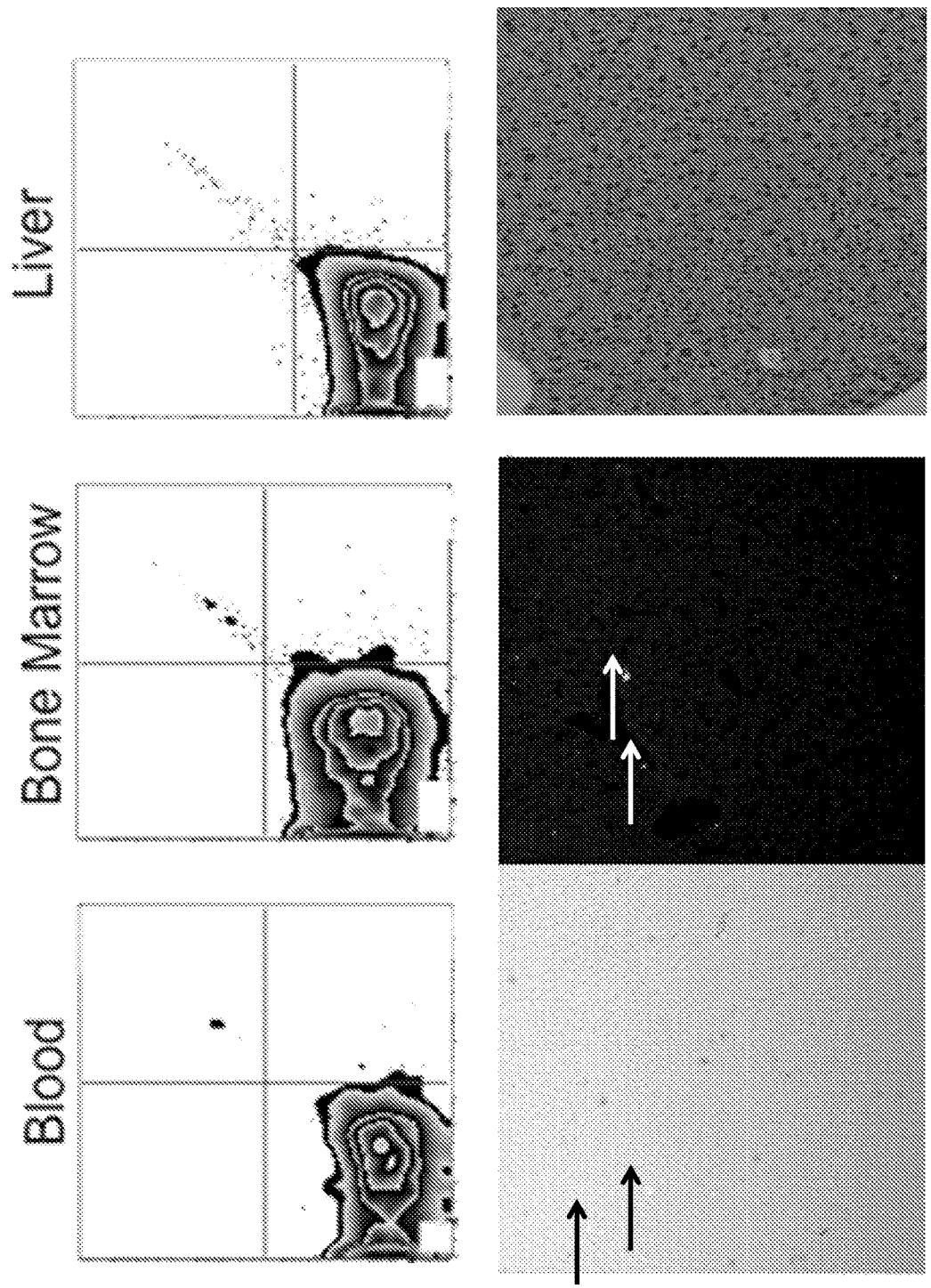
FIG. 9 is a panel of images showing in vivo engraftment of GFP+ transduced 4E5 CAR T cells into various organs by flow cytometry and immunofluorescence imaging.

$5 \times 10^6$ 4E5-BBz or 4E5-dZ transduced T-cells were injected into 6 non-tumor-bearing C57B1/6J mice. Mice were monitored for toxicity (clinical observation, weight, grooming) for 8 days and then sacrificed. The following tissues were harvested to evaluate histologically for injury: brain, heart, spleen, liver, kidney, bone marrow and skin. Tissues were reviewed by the Comparative Pathology Core at the University of Pennsylvania School of Veterinary Medicine and no tissue injury was identified in BBz-treated animals. Flow cytometry showed persistence of CAR-T in liver, blood, bone marrow and spleen as shown in the upper panel of FIG. 9. Immunofluorescence staining confirmed the presence of CAR-T cells in the tissues (lower panels of FIG. 9).

Figure 10:
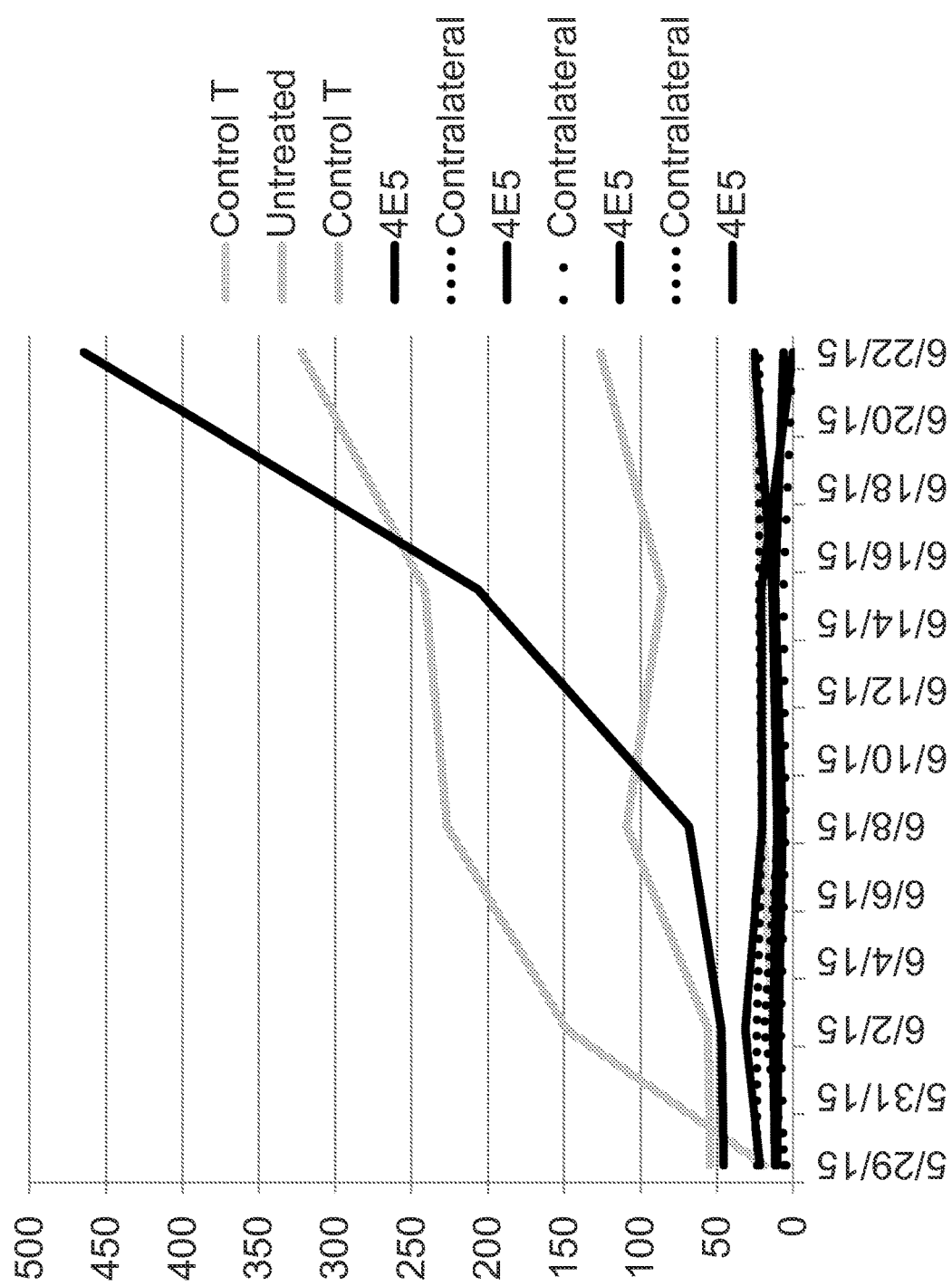
FIG. 10 is a graph showing tumor volume as measured by ultrasound.

$5 \times 10^6$ Hepal-6 cells suspended in matrigel were injected subcutaneously into the anterior abdominal wall on one side and $3 \times 10^6$ were injected into the contralateral side of 6 C57B1/6J mice. $5 \times 10^6$ 4E5 CAR-T cells were preactivated 1-2 days after electroporation using a PiggyBac transposon system, then co-cultured with mitomycin C-treated murine splenocytes as feeder cells. After co-culture, the 4E5 CAR-T cells were injected into the tumor burdened mice three times. Tumor volume was measured by ultrasound (FIG. 10). No clear impact of CAR-T cells on tumor growth was seen. However, tumor sizes were <50 mm³ and transduction efficiency was not clearly defined at the outset of the experiment.

The experiment was repeated with 6 mice, injecting $10 \times 10^6$ Hepal-6 into the right flank, waiting until tumor sizes reached 50 mm³. $5 \times 10^6$ 4E5 CAR-T cells were preactivated 1-2 days after electroporation using PiggyBac transposon system, cocultured with mitomycin C-treated murine splenocytes as feeder cells, and injected peritumorally into the mice three times on days 0, 7 and 14. Tumor volume was measured by calipers (½×L×W×W) every 3 days. 4E5-dz CAR-T (non-signaling) were used as negative control. As shown in FIG. 11, treated tumors regressed while control tumors slowly progressed.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated polynucleotide encoding an anti-glypican-3 (GPC3) antibody or antigen-binding fragment thereof comprising a heavy chain variable region and a light chain variable region, wherein the heavy chain variable region comprises SEQ ID NO: 1 and the light chain variable region comprises SEQ ID NO: 3.

2. An isolated anti-GPC3 antibody or antigen-binding fragment thereof comprising a heavy chain variable region and a light chain variable region, wherein the heavy chain variable region comprises SEQ ID NO: 2 and the light chain variable region comprises SEQ ID NO: 4.

3. The antigen-binding fragment of claim 2, wherein the antigen-binding fragment is selected from the group consisting of a Fab fragment, a F(ab')$_2$ fragment, a Fv fragment, and a single chain Fv (scFv).

4. A method of imaging or visualizing a sample taken from a normal or malignant tissue, the method comprising contacting the sample with a labeled anti-GPC3 antibody or antigen-binding fragment thereof, wherein the anti-GPC3 antibody or antigen-binding fragment thereof comprises a heavy chain variable region and a light chain variable region, wherein the heavy chain variable region comprises SEQ ID NO: 2 and the light chain variable region comprises SEQ ID NO: 4.

5. The method of claim 4, wherein the tissue comprises liver tissue.

6. The method of claim 4, wherein the antigen-binding fragment is a Fab or a scFv.

7. A method of inhibiting growth of a GPC3-expressing tumor cell, the method comprising contacting the tumor cell with an anti-GPC3 antibody or an antigen-binding fragment thereof comprising a heavy chain variable region and a light chain variable region, wherein an amino acid sequence of the heavy chain variable region comprises SEQ ID NO: 2 and the amino acid sequence of the light chain variable region comprises SEQ ID NO: 4.

8. A pharmaceutical composition comprising an effective amount of the isolated polynucleotide of claim 1.

9. A pharmaceutical composition comprising an effective amount of the isolated anti-GPC3 antibody or antigen-binding fragment thereof of claim 2.

10. An isolated nucleic acid sequence encoding a chimeric antigen receptor (CAR) comprising a glypican-3 (GPC3) binding domain, a transmembrane domain, a costimulatory signaling region, and a CD3 zeta signaling domain, wherein the isolated nucleic acid sequence that encodes the GPC3 binding domain comprises SEQ ID NO: 1 and SEQ ID NO: 3.

11. The isolated nucleic acid sequence of claim 10, wherein the encoded GPC3 binding domain comprises SEQ ID NO: 2 and SEQ ID NO: 4.

12. The isolated nucleic acid sequence of claim 10, wherein the co-stimulatory signaling domain comprises the intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof.

13. The isolated nucleic acid sequence of claim 11, wherein the encoded GPC3 binding domain is selected from the group consisting of a Fab fragment, a F(ab')$_2$ fragment, a Fv fragment, and a single chain Fv (scFv).

14. An isolated chimeric antigen receptor (CAR) comprising a GPC3 binding domain and a CD3 zeta signaling domain, wherein the GPC3 binding domain comprises SEQ ID NO: 2 and SEQ ID NO: 4.

15. The isolated CAR of claim 14, further comprising the sequence of a costimulatory signaling domain.

16. The isolated CAR of claim 15, wherein the co-stimulatory signaling domain is selected from the group consisting of CD27, CD28, 4-1BB 0X40, CD30, CD40, PD-1, ICOS, lymphocyte function-associated antigen-1 (LFA-1), CD2, CD7, LIGHT, NKG2C, B7-H3, and any combination thereof.

17. The isolated CAR of claim 14, wherein the GPC3 binding domain is a humanized antibody or antigen binding fragment thereof.

18. The isolated CAR of claim 14, wherein the GPC3 binding domain is selected from the group consisting of a Fab fragment, a F(ab')$_2$ fragment, a Fv fragment, and a single chain Fv (scFv).

19. A T cell comprising the isolated nucleic acid sequence of claim 10 or the CAR of claim 14.

20. A method of providing an anti-tumor immunity in a subject with a tumor that expresses glypican-3 (GPC3), the method comprising administering to the subject an effective amount of a genetically modified T cell comprising an isolated nucleic acid sequence encoding a chimeric antigen receptor (CAR) that comprises a glypican-3 (GPC3) binding domain, a 4-1BB co-stimulatory signaling domain, and a CD3 zeta signaling domain, wherein the GPC3 binding domain comprises SEQ ID NO: 2 and SEQ ID NO: 4.

21. The method of claim 20, wherein the T cell is an autologous T cell.

22. The method of claim 20, wherein the subject is a human.

23. A method of treating a glypican-3 (GPC3)-expressing liver cancer in a subject, the method comprising administering to the subject an effective amount of a genetically modified T cell comprising an isolated nucleic acid sequence encoding a chimeric antigen receptor (CAR) that comprises a GPC3 binding domain, a 4-1BB co-stimulatory signaling domain, and a CD3 zeta signaling domain, wherein the GPC3 binding domain comprises SEQ ID NO: 2 and SEQ ID NO: 4.

* * * * *